(12) United States Patent
John et al.

(10) Patent No.: US 11,241,356 B2
(45) Date of Patent: Feb. 8, 2022

(54) WALKING ASSISTANCE APPARATUS

(71) Applicant: Panasonic Intellectual Property Management Co., Ltd., Osaka (JP)

(72) Inventors: Stephen William John, Nara (JP); Jun Ozawa, Nara (JP); Mayumi Komatsu, Kyoto (JP); Kenta Murakami, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 738 days.

(21) Appl. No.: 16/121,243

(22) Filed: Sep. 4, 2018

(65) Prior Publication Data

US 2018/0369057 A1 Dec. 27, 2018

Related U.S. Application Data

(63) Continuation of application No. PCT/JP2017/021586, filed on Jun. 12, 2017.

(30) Foreign Application Priority Data

Jul. 13, 2016 (JP) .............................. JP2016-138503
Mar. 10, 2017 (JP) .............................. JP2017-046620

(51) Int. Cl.
*A61H 3/00* (2006.01)
*A61B 5/00* (2006.01)
(Continued)

(52) U.S. Cl.
CPC ............. *A61H 3/00* (2013.01); *A61B 5/1038* (2013.01); *A61B 5/112* (2013.01); *A61B 5/4836* (2013.01);
(Continued)

(58) Field of Classification Search
CPC .... A61H 3/00; A61H 2003/007; A61H 3/008; A61B 5/112; A61B 5/6828; A61B 5/6829; B25J 9/0006
See application file for complete search history.

(56) References Cited

U.S. PATENT DOCUMENTS

2006/0069336 A1   3/2006  Krebs et al.
2013/0046218 A1*  2/2013  Wiggin ................. A61F 5/0102
                                                            602/16
(Continued)

FOREIGN PATENT DOCUMENTS

JP   2007-054086    3/2007
JP   2010-110381    5/2010
(Continued)

OTHER PUBLICATIONS

International Search Report of PCT application No. PCT/JP2017/021586 dated Sep. 5, 2017.
(Continued)

*Primary Examiner* — Margaret M Luarca
*Assistant Examiner* — Cana A Gallegos
(74) *Attorney, Agent, or Firm* — Wenderoth, Lind & Ponack, L.L.P.

(57) ABSTRACT

A walking assistance apparatus includes a knee fastener, a heel fastener, a first wire and a second wire connected to the knee fastener and the heel fastener, a first motor connected to the first wire, a second motor connected to the second wire, and a control circuit that controls the first motor and the second motor. The first wire is connected to a first position included in a right-half region of the heel fastener. The second wire is connected to a second position included in a left-half region of the heel fastener. The control circuit acquires gait information of the user, and, based on the gait information, the control circuit controls the first motor to reduce a length of the first wire and the second motor to (Continued)

reduce a length of the second wire at a predetermined timing.

15 Claims, 24 Drawing Sheets

(51) Int. Cl.
*A61B 5/103* (2006.01)
*A61B 5/11* (2006.01)
*A61H 1/02* (2006.01)

(52) U.S. Cl.
CPC .......... *A61B 5/6812* (2013.01); *A61B 5/6829* (2013.01); *A61H 1/0266* (2013.01); *A61H 2003/007* (2013.01); *A61H 2201/1207* (2013.01); *A61H 2201/14* (2013.01); *A61H 2201/165* (2013.01); *A61H 2201/1642* (2013.01); *A61H 2201/5061* (2013.01); *A61H 2205/12* (2013.01); *A61H 2230/00* (2013.01)

(56) References Cited

U.S. PATENT DOCUMENTS

| | | | |
|---|---|---|---|
| 2014/0277739 A1* | 9/2014 | Kornbluh | G16Z 99/00 700/260 |
| 2015/0342819 A1 | 12/2015 | Shimada et al. | |
| 2017/0202724 A1* | 7/2017 | De Rossi | A61F 5/0102 |

FOREIGN PATENT DOCUMENTS

| | | |
|---|---|---|
| JP | 2010-110543 | 5/2010 |
| JP | 2014-226151 | 12/2014 |
| JP | 2015-223295 | 12/2015 |

OTHER PUBLICATIONS

Hiroshi Saito, Walking, 4th in Kinematics of lower limb, Kinematics for prosthetic limb, "The important point of prosthetic limb", IGAKU-SHOIN Ltd., ver.4, Jan. 1978, pp. 25-27 (Partial Translation).

* cited by examiner

FIG. 9

|    | TIME       | SENSOR SIGNAL |
|----|------------|---------------|
|    | ...        | ...           |
| 1  | 0:10:3.143 | ON            |
| 2  | 0:10:3.622 | OFF           |
| 3  | 0:10:3.952 | ON            |
| 4  | 0:10:4.221 | OFF           |
| 5  | 0:10:4.793 | ON            |
| 6  | 0:10:5.102 | OFF           |
| 7  | 0:10:5.602 | ON            |
| 8  | 0:10:6.122 | OFF           |
| 9  | 0:10:6.388 | ON            |
| 10 | 0:10:6.810 | OFF           |
|    | ...        | ...           |

810 msec
841 msec
809 msec
786 msec

AVERAGE 820 msec

FIG. 13
(a)
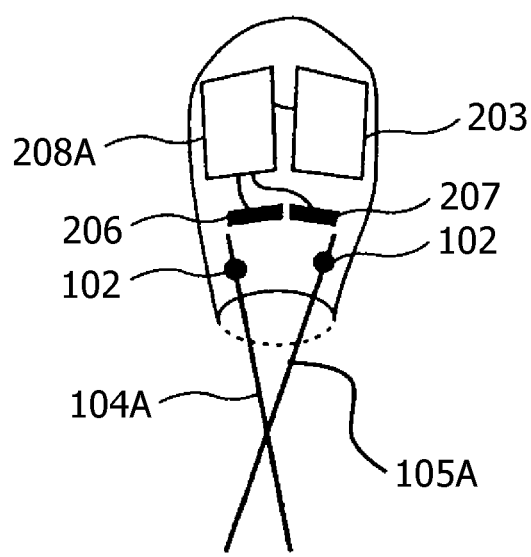
(b)
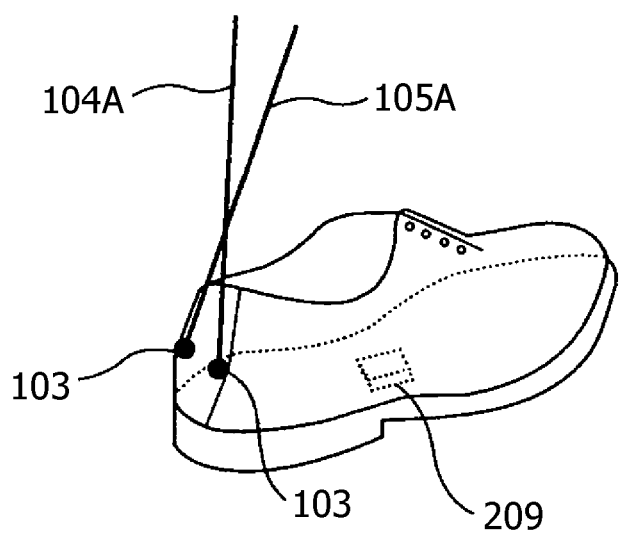

FIG. 14
(a-1) PARALLEL TYPE
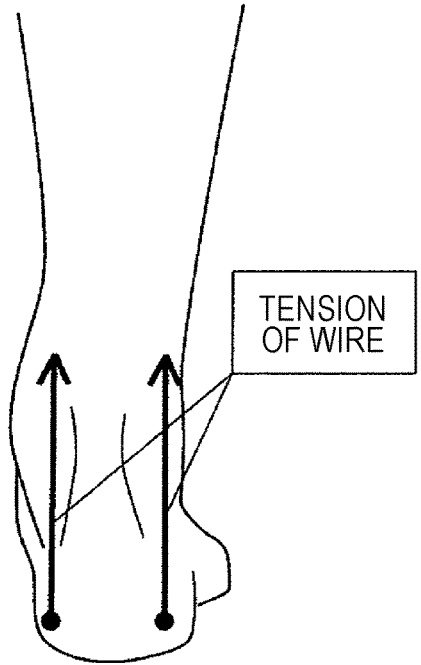
TENSION OF WIRE
(b-1) CROSS TYPE
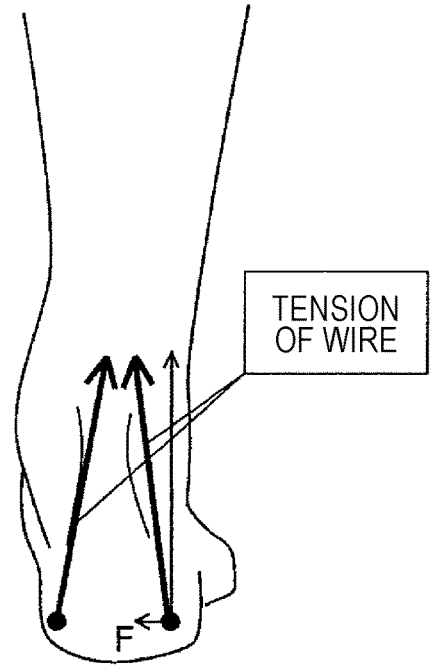
TENSION OF WIRE
(a-2) PARALLEL TYPE
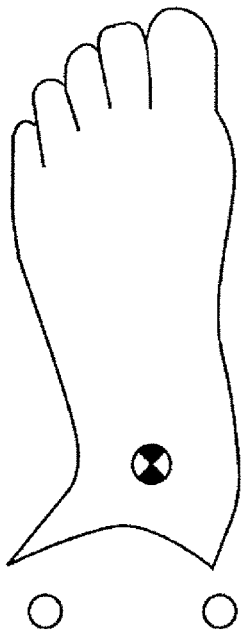
(b-2) CROSS TYPE
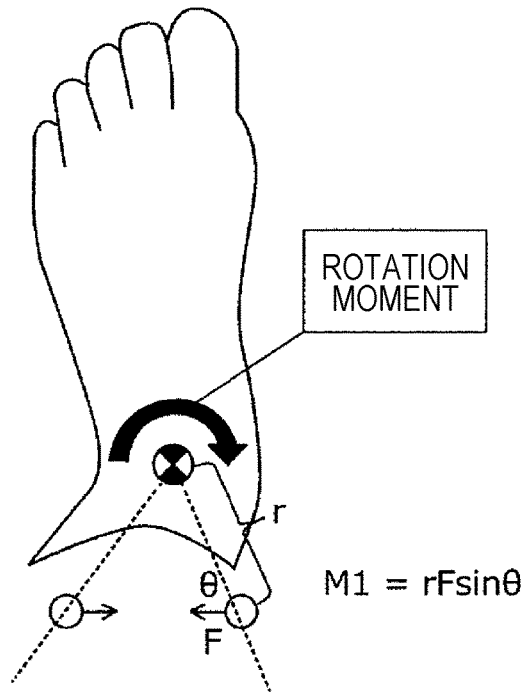
ROTATION MOMENT
$M1 = rF\sin\theta$ FIG. 21
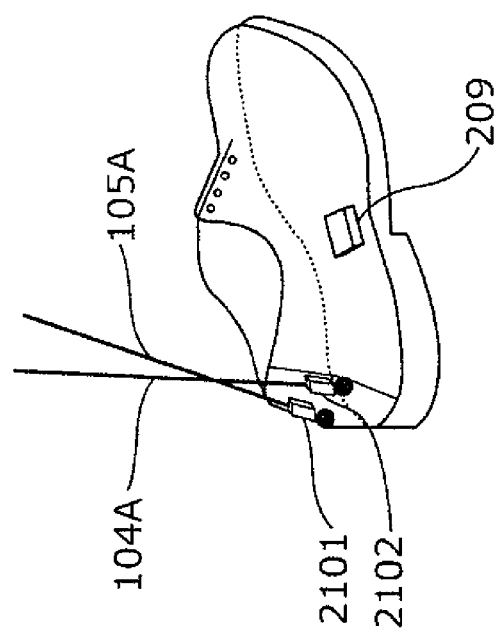
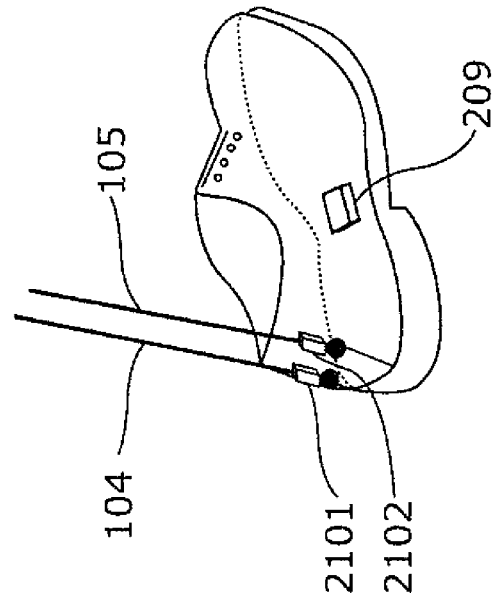

WALKING ASSISTANCE APPARATUS

BACKGROUND

1. Technical Field

The present disclosure relates to a walking assistance apparatus that assists in walking.

2. Description of the Related Art

Japanese Unexamined Patent Application Publication No. 2014-226151 describes a technology related to an ankle assistance apparatus that is to be worn on an ankle of a user and that utilizes the driving force of a motor.

SUMMARY

However, existing ankle assistance apparatuses, which perform assistance by using one motor for one leg, can only perform assistance in a predetermined rotation direction.

One non-limiting and exemplary embodiment provides a walking assistance apparatus that assists in flexion of an ankle by using multiple wires and generates tensions in the wires while adjusting the lengths of the wires in accordance with a motion of the ankle in a walking style of a user, and thereby realizes natural assistance.

In one general aspect, the techniques disclosed here feature a walking assistance apparatus including a knee fastener to be worn on a knee of a leg of a user, a heel fastener to be worn on a heel of the leg of the user, a first wire connected to the knee fastener and the heel fastener and to be located on a back side of the user, a second wire connected to the knee fastener and the heel fastener and to be located on the back side of the user, a first motor connected to the first wire, a second motor connected to the second wire, and a control circuit that controls the first motor and the second motor. The first wire is connected to a first position included in a right-half region of the heel fastener. The second wire is connected to a second position included in a left-half region of the heel fastener. The control circuit acquires gait information of the user, and, based on the gait information, the control circuit controls the first motor to reduce a length of the first wire and the second motor to reduce a length of the second wire at a predetermined timing.

It should be noted that general or specific embodiments may be implemented as a system, a method, an integrated circuit, a computer program, a computer-readable recording medium, or any selective combination thereof. A computer readable recording medium includes, for example, a non-volatile recording media, such as a compact disc-read only memory (CD-ROM).

With the present disclosure, it is possible to realize natural assistance by generating tensions while adjusting the lengths of the wires in accordance with the motion of an ankle in the walking style of a user.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 9 illustrates a signal history from a foot sensor;

FIG. 13 shows external views of a second embodiment;

FIG. 14 illustrates advantages of a cross-type wire arrangement;

FIG. 21 is an external view when force sensors are attached;

DETAILED DESCRIPTION

Figure 1A:
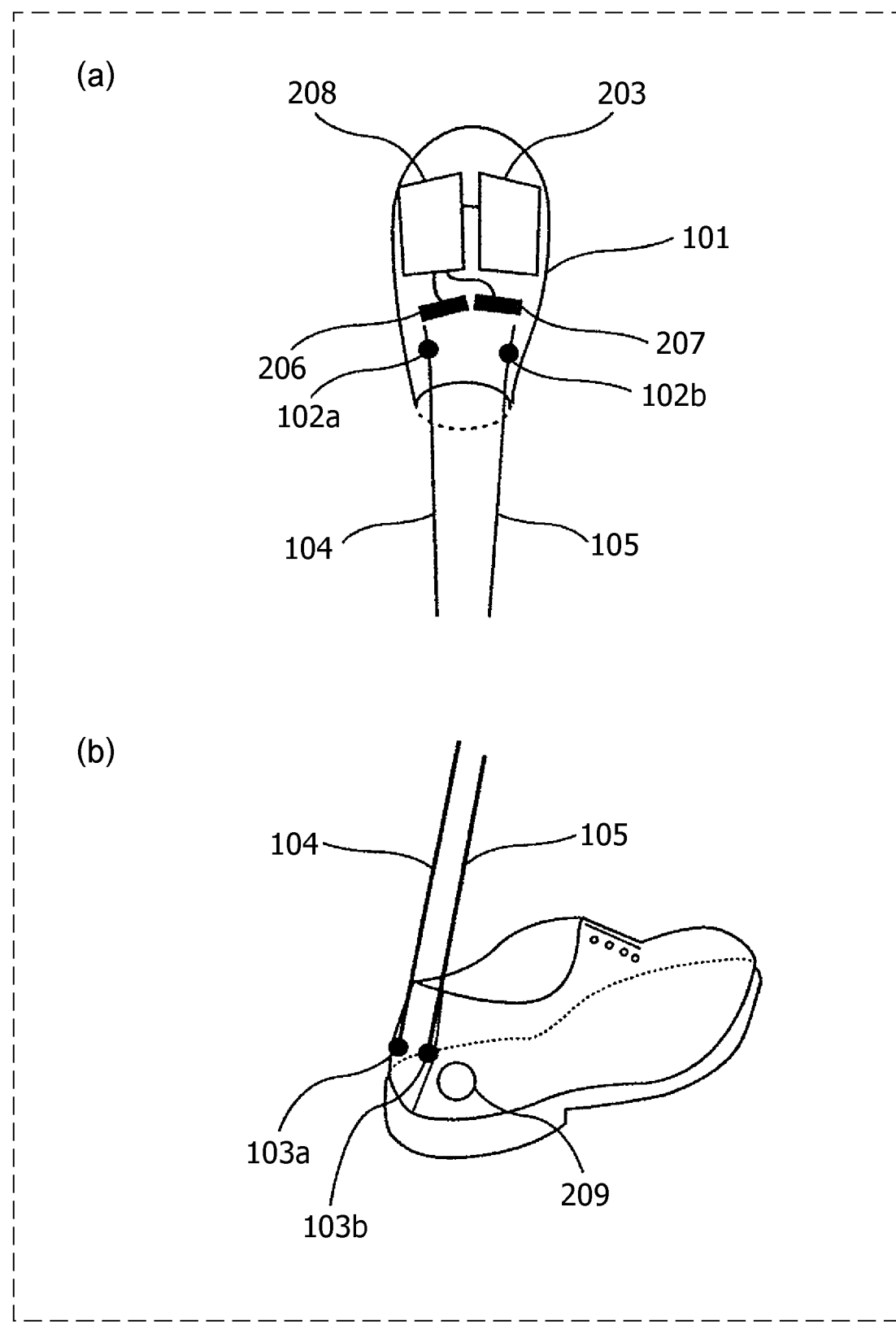
FIG. 1A shows external views of a first embodiment.

Underlying Knowledge Forming Basis of the Present Disclosure

The inventors found that the ankle assistance apparatus described in "Description of the Related Art" has the following problem.

When a person is walking, an ankle moves while changing the rotation direction in accordance with the angle of the ankle joint. Thus, the ankle assistance apparatus described in Japanese Unexamined Patent Application Publication No. 2014-226151, which has a motor with one degree of freedom, cannot perform natural assistance. Moreover, the angle of the rotation axis of an ankle differs depending on the walking style of an individual, and it is difficult to adapt to the difference by using a motor with one degree of freedom.

In order to solve the problem, a walking assistance apparatus according to an aspect of the present disclosure includes a knee fastener to be worn on a knee of a leg of a user, a heel fastener to be worn on a heel of the leg of the user, a first wire connected to the knee fastener and the heel fastener and to be located on a back side of the user, a second wire connected to the knee fastener and the heel fastener and to be located on the back side of the user, a first motor connected to the first wire, a second motor connected to the second wire, and a control circuit that controls the first motor and the second motor. The first wire is connected to a first position included in a right-half region of the heel fastener. The second wire is connected to a second position included in a left-half region of the heel fastener. The control circuit acquires gait information of the user, and, based on the gait information, the control circuit controls the first motor to reduce a length of the first wire and the second motor to reduce a length of the second wire at a predetermined timing.

The walking assistance apparatus can assist a user in walking by using the first wire and the second wire, which are disposed on the left side and the right side of the leg of the user. Thus, the walking assistance apparatus can generate torques for assistance in a direction in which the ankle of the user is flexed and in a direction in which the ankle is abducted. Therefore, it is possible to realize natural assistance by generating tensions while adjusting the lengths of the wires in accordance with the motion of the ankle in the walking style of the user.

The gait information of the user may include information on a gait cycle of the user, and the control circuit may control the first motor to reduce the length of the first wire and the second motor to reduce the length of the second wire in a period of 40% or more and 60% or less of the gait cycle of the user as the predetermined timing, where a percentage of the gait cycle is defined such that a time when a foot of the user contacts a ground is 0% and a time when the foot of the user contacts the ground next time is 100%.

In this case, the walking assistance apparatus can assist the user in flexing the ankle at the timing at which the user flexes the ankle.

The first wire may be disposed on an inside of the leg, the second wire may be disposed on an outside of the leg, and an elongation of the first wire may be larger than an elongation of the second wire.

In this case, it is possible to effectively reduce breakage of the first wire, because the elongation of the first wire, which is disposed inside and to which a larger load tends to be applied than to the second wire, is larger than the elongation of the second wire. Moreover, it is possible to reduce the cost of the second wire, because the elongation of the second wire is smaller than the elongation of the first wire.

The first wire may be disposed on an inside of the leg, the second wire may be disposed on an outside of the leg, and a maximum torque of the first motor may be larger than a maximum torque of the second motor.

In this case, it is easy to make a tension applied to the first wire larger than a tension applied to the second wire, because the maximum torque of the first motor connected to the first wire, which is disposed inside and to which a larger load tends to be applied than to the second wire, is larger than the maximum torque of the second motor connected to the second wire. Moreover, it is possible to reduce the cost of the second motor, because the maximum torque of the second motor is smaller than the maximum torque of the first motor.

The first wire may be disposed on an inside of the leg, the second wire may be disposed on an outside of the leg, and a maximum speed of the first wire may be higher than a maximum speed of the second wire.

In this case, it is possible to increase the response in speed of assisting in adduction of the ankle of the user, because the maximum speed of the first wire, which is disposed inside and whose assistance amount is a larger than the assistance amount of the second wire, is higher than the maximum speed of the second wire. Therefore, it is possible to effectively assist the user in walking.

A distance between the first position and the second position may be 20 mm or larger.

In this case, it is possible to effectively generate a force with a moment in the leftward or rightward inclination.

The first wire may be connected to a third position included in a left-half region of the knee fastener, and the second wire may be connected to a fourth position included in a right-half region of the knee fastener.

In this case, it is possible to effectively generate a force with a moment in the leftward or rightward rotation direction.

The control circuit further may acquire information on a gait cycle of the user by using the gait information, and based on the information on the gait cycle, the control circuit may control the first motor to reduce the length of the first wire and the second motor to reduce the length of the second wire in a period of a gait cycle in a next walking of the user.

In this case, it is possible to assist the user in walking in accordance with the gait cycle of the user.

The control circuit may further acquire winding amounts of the first wire and the second wire by using the first motor and the second motor, and in accordance with differences between first criteria that specify a length of the first wire and a length of the second wire for each gait cycle and the winding amounts of the first wire and the second wire, the control circuit may control the first motor to reduce the length of the first wire and the second motor to reduce the length of the second wire in a predetermined period of a gait cycle in a next walking of the user.

In this case, it is possible to assist the user in walking with an appropriate ankle rotation amount.

The walking assistance apparatus may further include a first spring disposed between the first wire and the heel fastener, and a second spring disposed between the second wire and the heel fastener.

In this case, it is possible to perform control with rigidity.

The control circuit may acquire tensions of the first wire and the second wire, and in accordance with differences between second criteria that specify a tension of the first wire and a tension of the second wire for each gait cycle and the tensions of the first wire and the second wire, the control circuit may control the first motor to reduce the length of the first wire and the second motor to reduce the length of the second wire in a predetermined period of a gait cycle in a next walking of the user.

In this case, it is possible to assist the user in walking with an appropriate force.

The walking assistance apparatus may further include a first force sensor disposed on the first wire, and a second force sensor disposed on the second wire.

The walking assistance apparatus may further include a rotation detector that detects a rotation direction of the user, and based on the rotation direction of the user and the gait information, the control circuit may control the first motor to reduce the length of the first wire and the second motor to reduce the length of the second wire at a predetermined timing.

In these cases, it is possible to appropriately assist the user in walking even when the user changes direction rightward or leftward during walking.

If the first wire is longer than the second wire when the first motor and the second motor are not driven and the user is walking, the control circuit may control the first motor and the second motor to make the first wire longer than the second wire; and if the first wire is shorter than the second wire when the first motor and the second motor are not driven and the user is walking, the control circuit may control the first motor and the second motor to make the first wire shorter than the second wire.

In this case, it is possible to appropriately assist a user in walking in accordance with the walking style of the user.

A walking assistance apparatus according to another aspect of the present disclosure includes a first wire including a first end and a second end, a second wire including a third end and a fourth end, a first motor connected to the first end, a second motor connected to the third end, a sensor, and a controller. (a-1) The first motor and the second motor are included in a first belt to be worn around a knee of a first leg of a user, and the second end and the fourth end are fixed to a second belt to be worn around an ankle of the first leg or fixed to a shoe to be worn on the first leg; or (a-2) the first motor and the second motor are included in the second belt or the shoe, and the second end and the fourth end are fixed to the first belt. (b) The sensor detects a ground contact at an i-th time and at an (i+1)-th time after the i-th time, the ground contact being a change from a first state in which the first leg is separated from a ground to a second state in which the first leg is in contact with the ground, and the sensor does not detect the ground contact between the i-th time and the (i+1)-th time, where 1≤i≤n where i is a natural number and n is a natural number greater than 1. (c) If the sensor detects the ground contact at the (i+1)-th time, (c-1) the controller controls the first motor to wind the first wire to make a first tension of the first wire between the first end and the first motor in a period from the (i+1)-th time to 40% or more and 60% or less of an average gait cycle be larger than a second tension of the first wire between the first end and the first motor at the (i+1)-th time; and (c-2) the controller controls the second motor to wind the second wire to make a third tension of the second wire between the third end and the second motor in the period from the (i+1)-th time to 40% or more and 60% or less of the average gait cycle be larger than a fourth tension of the second wire between the third end and the second motor at the (i+1)-th time. (d) The average gait cycle is determined based on a difference between the (i+1)-th time and the i-th time.

First Embodiment

FIG. 1A shows external views of a walking assistance apparatus 100. Part (a) of FIG. 1A is an external view of a portion of the walking assistance apparatus 100 to be worn on a knee of a user. Part (b) of FIG. 1A is an external view of a portion of the walking assistance apparatus 100 to be worn on an ankle of the user.

The walking assistance apparatus 100 illustrated in FIG. 1A includes a knee belt 101, knee fasteners 102a and 102b, heel fasteners 103a and 103b, a first wire 104, and a second wire 105.

The knee belt 101 is to be worn around a knee of a user. The knee fasteners 102a and 102b are disposed at specific positions on the knee belt 101. Accordingly, when the user wears the knee belt 101 on the knee, the knee fasteners 102a and 102b are fixed to the knee of the user. The knee fasteners 102a and 102b are worn on a leg of the user.

The knee belt 101 may be a simple belt or may be a belt that can be fastened with a tape (a hook and loop fastener or a Velcro tape).

The heel fasteners 103a and 103b are to be worn on the heel of the user. The heel fasteners 103a and 103b illustrated in FIG. 1A are disposed at specific positions on a shoe. Accordingly, when the user puts on the shoe, the heel fasteners 103a and 103b are fixed to the heel of the user who wears the shoe.

The heel fastener 103a may be a first buckle. The first wire 104 may be connected to the heel fastener 103a by linking an opening portion, which is formed at one end of the first wire 104, to the first buckle. The heel fastener 103b may be a second buckle. The second wire 105 may be connected to the heel fastener 103b by linking an opening portion, which is formed at one end of the second wire 105, to the second buckle.

That is, the heel fasteners 103a and 103b need not be directly fixed to the heel of the user. For another example, the heel fasteners 103a and 103b may be disposed at specific positions on an ankle belt, which is directly worn around the ankle of the user and fixed to the ankle of the user. In this case, when the user wears the ankle belt around the ankle, the heel fasteners 103a and 103b are fixed to the heel of the user.

The first wire 104 connects the knee fastener 102a and the heel fastener 103a to each other. The second wire 105 connects the knee fastener 102b and the heel fastener 103b to each other. The first wire 104 and the second wire 105 are located on the back side of the user.

For example, one end of the first wire 104 is fixed to the heel fastener 103a, and the other end of the first wire 104 is fixed to a motor 206 (described below). The first wire 104 may be connected to the knee fastener 102a at a position between the one end and the other end of the first wire 104.

The first wire 104 is supported in such a way that a portion of the first wire 104 between the one end and the other end of the first wire 104 can slide over the knee fastener 102a in the longitudinal direction of the first wire 104. The one end of the first wire 104 is also referred to as a first end, and the other end of the first wire 104 is also referred to as a second end. The knee fastener 102a may be a first pulley. The first pulley may be attached to the knee belt 101 by sewing the first pulley at a first predetermined position on the knee belt 101. The first pulley may support the first wire 104 in such a way that the first wire 104 can freely slide over the first pulley.

Likewise, one end of the second wire 105 is fixed to the heel fastener 103b, and the other end of the second wire 105 is fixed to a motor 207 (described below). The second wire 105 may be connected to the knee fastener 102b at a position between the one end and the other end of the second wire 105. The second wire 105 is supported in such a way that a portion of the second wire 105 between the one end and the other end of the second wire 105 can slide over the knee fastener 102b in the longitudinal direction of the second wire 105. The one end of the second wire 105 is also referred to as a third end, and the other end of the second wire 105 is also referred to as a fourth end. The knee fastener 102b may be a second pulley. The second pulley may be attached to the knee belt 101 by sewing the second pulley at a second predetermined position on the knee belt 101. The second pulley may support the second wire 105 in such a way that the second wire 105 can freely slide over the second pulley.

Figure 1B:
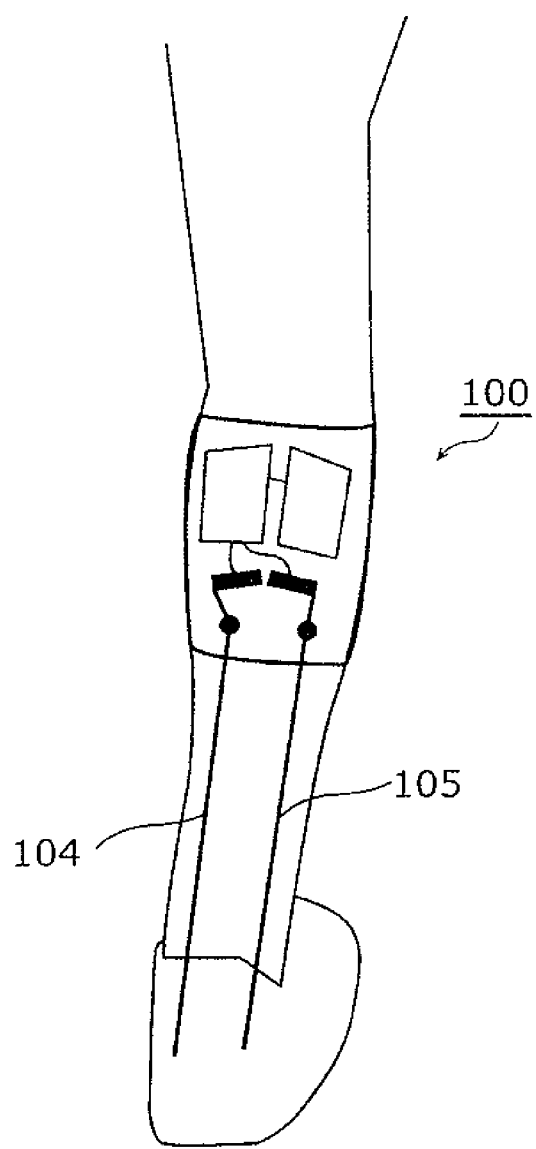
FIG. 1B is an external view of the first embodiment.

FIG. 1B is a rear view of the right leg of a user who wears the walking assistance apparatus 100. When seen from behind the user, the first wire 104 is positioned inside. That is, when seen from behind the user, the first wire 104 is connected to the heel fastener 103a, which is one of the heel fasteners 103a and 103b that is positioned on the left side, that is, inside. A position on the heel fastener 103a to which the first wire 104 is connected is also referred to as a first position. When a region including the heel fasteners 103a and 103b is regarded as a heel fastener 103, the first wire 104 is connected to a left-half region of the heel fastener 103.

When seen from behind the user, the second wire 105 is positioned outside. That is, when seen from behind the user, the second wire 105 is connected to the heel fastener 103b, which is one of the heel fasteners 103a and 103b that is positioned on the right side, that is, outside. A position on the heel fastener 103b to which the second wire 105 is connected is also referred to as a second position. When a region including the heel fasteners 103a and 103b is regarded as the heel fastener 103, the second wire 105 is connected to a right-half region of the heel fastener 103.

The knee belt 101 includes the motors 206 and 207. Each of the motors 206 and 207 includes a shaft or a pulley connected to a shaft. Each of the first wire 104 and the second wire 105 is connected to the shaft or the pulley, and the rotation torque thereof is controlled. It is possible to change the length of the first wire 104 by winding or unwinding the first wire 104 by rotating the motor 206. It is possible to change the length of the second wire 105 by winding or unwinding the second wire 105 by rotating the motor 207.

The tension of the first wire 104 increases when the first wire 104 is wound by rotating the motor 206. The tension of the second wire 105 increases when the second wire 105 is wound by rotating the motor 207. As a result, a force is generated in a direction such that the distance between the knee and the heel is reduced, and thereby it is possible to assist in a motion of an ankle during walking by generating.

Tensions are generated in the first wire 104 and the second wire 105 by using the motors 206 and 207, which are independent from each other. For example, by setting the tensions of the first wire 104 and the second wire 105 at different values, it is possible to generate a force related to the leftward or rightward inclination of the heel and to assist in the motion of the ankle during walking.

Figure 2:
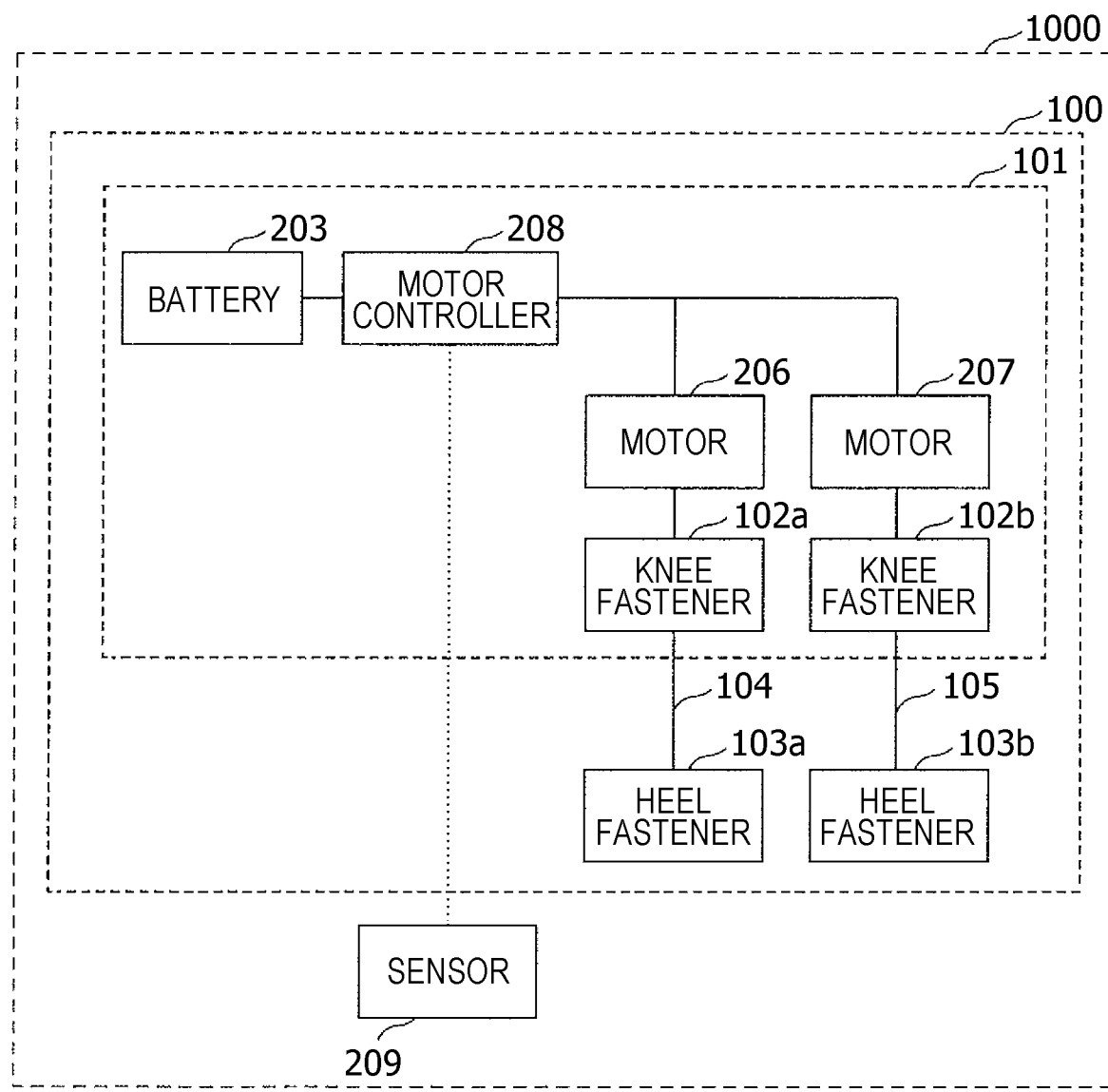
FIG. 2 illustrates a hardware configuration of the first embodiment.

FIG. 2 is an example of a functional block diagram of a walking assistance system 1000. The walking assistance system 1000 illustrated in FIG. 2 includes the knee belt 101, the heel fasteners 103a and 103b, and a sensor 209. The walking assistance apparatus 100 includes the knee belt 101 and the heel fasteners 103a and 103b.

The knee belt 101 includes a battery 203, a motor controller 208, the motors 206 and 207, and the knee fasteners 102a and 102b. The battery 203 is electrically connected to the motor controller 208 and the motors 206 and 207.

One end of the first wire 104 is fixed to the heel fastener 103a, and the other end of the first wire 104 is fixed to the motor 206. The first wire 104 is connected to the knee fastener 102a at a position between the one end and the other end of the first wire 104. One end of the second wire 105 is fixed to the heel fastener 103b, and the other end of the second wire 105 is fixed to the motor 207. The second wire 105 is connected to the knee fastener 102b at a position between the one end and the other end of the second wire 105.

The knee fastener 102a is connected to the first wire 104 in a left-half region of the knee fastener 102. The knee fastener 102b is connected to the second wire 105 in a right-half region of the knee fastener 102.

The heel fastener 103a is fixed to the first wire 104 in a left-half region of the heel fastener 103. The heel fastener 103b is fixed to the second wire 105 in a right-half region of the heel fastener 103.

The sensor 209 acquires gait information of a user. For example, the sensor 209 is attached to a position near a heel of a person. An example of the sensor 209 is a pressure sensor. The pressure sensor generates a signal that indicates whether the heel is in contact with the ground. The signal of the pressure sensor represents a measured pressure value. For example, a period when a pressure value of a predetermined level or higher is measured is a period when the heel is in contact with the ground. Other examples of the sensor include a foot switch, an angular velocity sensor, and an angle sensor.

The motor controller 208 acquires gait information of a user from the sensor 209 and outputs a controls signal to the motors 206 and 207. An example of the gait information is a sensor value measured by the sensor 209 or information on a gait cycle. The motor controller 208 may acquire the sensor value of the sensor 209 as gait information and calculate a gait cycle (described below). Alternatively, the motor controller 208 may acquire, as gait information, information on a gait cycle that is calculated by using the sensor value.

The motor controller 208 is an example of a control circuit.

The motors 206 and 207 respectively control winding, unwinding, and the tensions of the first wire 104 and the second wire 105 based on control signals. Examples of the control signals include winding amounts and unwinding amounts of the first wire 104 and the second wire 105 and timings at which the first wire 104 and the second wire 105 are to be driven.

Gait Cycle

Figure 3:
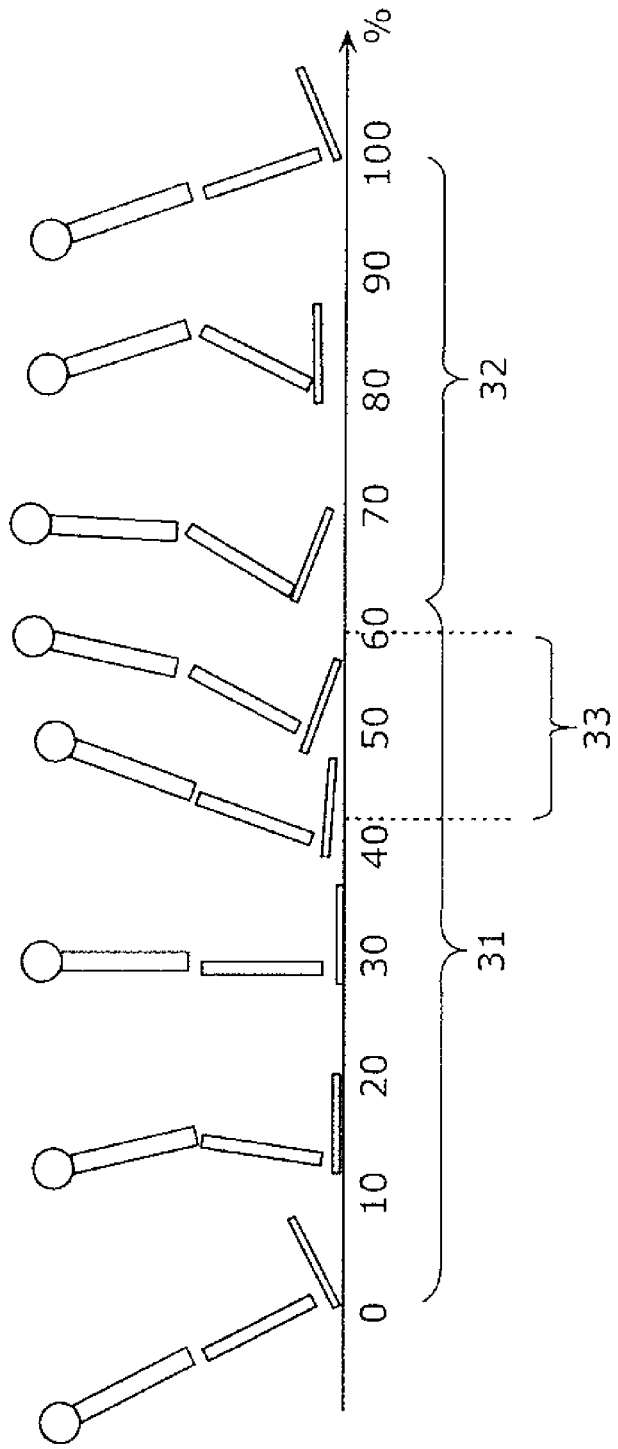
FIG. 3 illustrates the timing of assisting an ankle.

Referring to FIG. 3, the timing of assisting an ankle during walking will be described. FIG. 3 illustrates an example of a gait cycle. FIG. 3 is a side view of a model of a user during the gait cycle. In FIG. 3, a proportion of the gait cycle focused on one foot of a user is represented by %.

At 0% shown in FIG. 3, the foot of the user is in contact with the ground. In FIG. 3, the period from 0% to 60% is also referred to as a stance phase 31 and the period from 60% to 0% is also referred to as a swing phase 32. That is, in the example of a gait cycle, a state in which user is walking is represented by a value in the range 0 to 100%, where 0% is a time when a foot of the user contacts the ground and 100% is the next time when the foot of the user contacts the ground. For example, a gait cycle may correspond to a period from a time when the foot of the user contacts the ground to the next time when the foot of the user contacts the ground. To be specific, if the period from the time when the foot of the user contacts the ground to the next time when the foot of the user contacts the ground is 1 sec, a time that is 0.5 sec after the foot of the user first contacts the ground is represented as 50% of the gait cycle.

To be more specific, a time when the heel of one foot of the user contacts the ground is 0% of the gait cycle. Subsequently, the sole of the user contacts the ground, and then the toe of the user contacts the ground. Next, the heel of the user leaves the ground, the toe of the user strikes the ground, and the foot of the user leaves the ground. A time when the heel of the user contacts the ground again is 100% of the gait cycle.

When the user is walking, the ankle flexes in a period from the time when the heel of the user contacts the ground to the time when the toe of the user leaves the ground. In a period 33 of flexion of the ankle, the distance between the knee and the heel is short. Therefore, by assisting in the flexion by using the tensions of the wires, it is possible to assist the user in walking. Rotational motions of an ankle include extension and flexion. Flexion of an ankle is a motion in which the ankle joint is rotated in a direction such that the toe points downward with respect to the body of a person. Extension of an ankle is a motion with which the ankle joint is rotated in a direction such that the toe points upward with respect to the body of a person.

In the period when the ankle flexes, the walking assistance apparatus 100 assists the user in walking by generating a force in a direction such that the distance between the knee and the heel decreases. An example of the period when the ankle flexes is the period of 40% or more and 60% or less of a gait cycle or a period of 50% or more and 60% or less of the gait cycle. That is, the motor controller 208 acquires information on the gait cycle of the user by using gait information. By using the information on the gait cycle, the motor controller 208 controls the motor 206 to reduce the length of the first wire 104 and the motor 207 to reduce the length of the second wire 105 in a predetermined period in a gait cycle in the next walking of the user. An example of the predetermined period in the gait cycle is the period of 40% or more and 60% or less of the gait cycle or the period of 50% or more and 60% or less of the gait cycle. Therefore, it is possible to assist the user in walking in accordance with the gait cycle of the user.

Experiment Results

Experiment results showing a difference in gait between users will be described.

Figure 4:
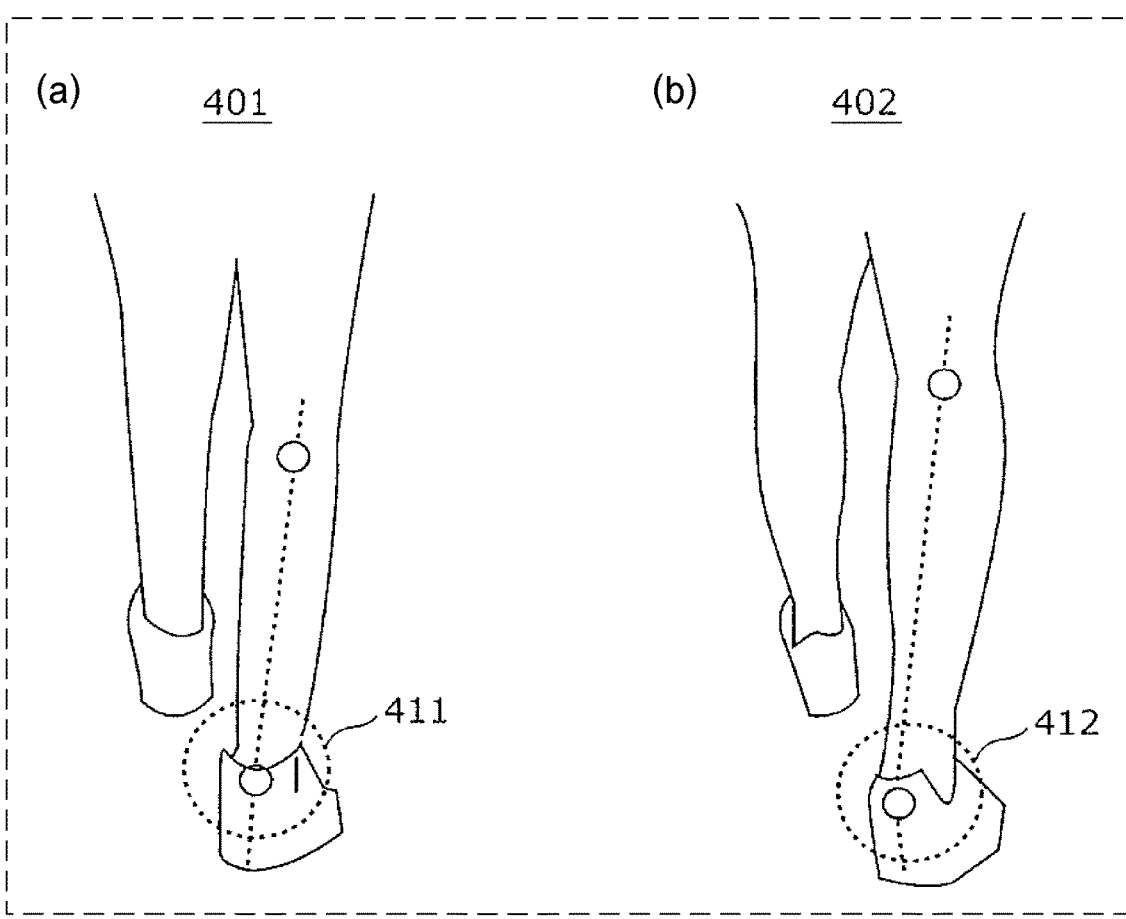
FIG. 4 illustrates a difference in walking style between subjects.

Human walking, which depends on the muscle mass, the bone length, the bone angle, and the manner of walking, differs considerably between individuals. FIG. 4 shows rear views of subjects during walking. Part (a) of FIG. 4 shows a subject 401, and part (b) of FIG. 4 shows a subject 402. When the subject 401 and the subject 402 are seen from behind, an angle 411 of an ankle of the subject 401 differs from an angle 412 of an ankle of the subject 402.

To be specific, the angle 411 of the ankle of the subject 401 at the ankle joint is substantially straight, whereas the angle 412 of the ankle of the subject 402 at the ankle joint is bent outward. The term "outward" refers to a direction such that the foot is open outward.

The ankle of the subject 402 is abducted further than the ankle of the subject 401. In other words, the abduction angle of the ankle of the subject 401 is smaller than the abduction angle of the ankle of the subject 402.

That is, it can be seen that, when a person is walking, the ankle is moving also in the abduction direction or the adduction direction, each of which is different from the direction in which the leg moves forward and backward.

Figure 5:
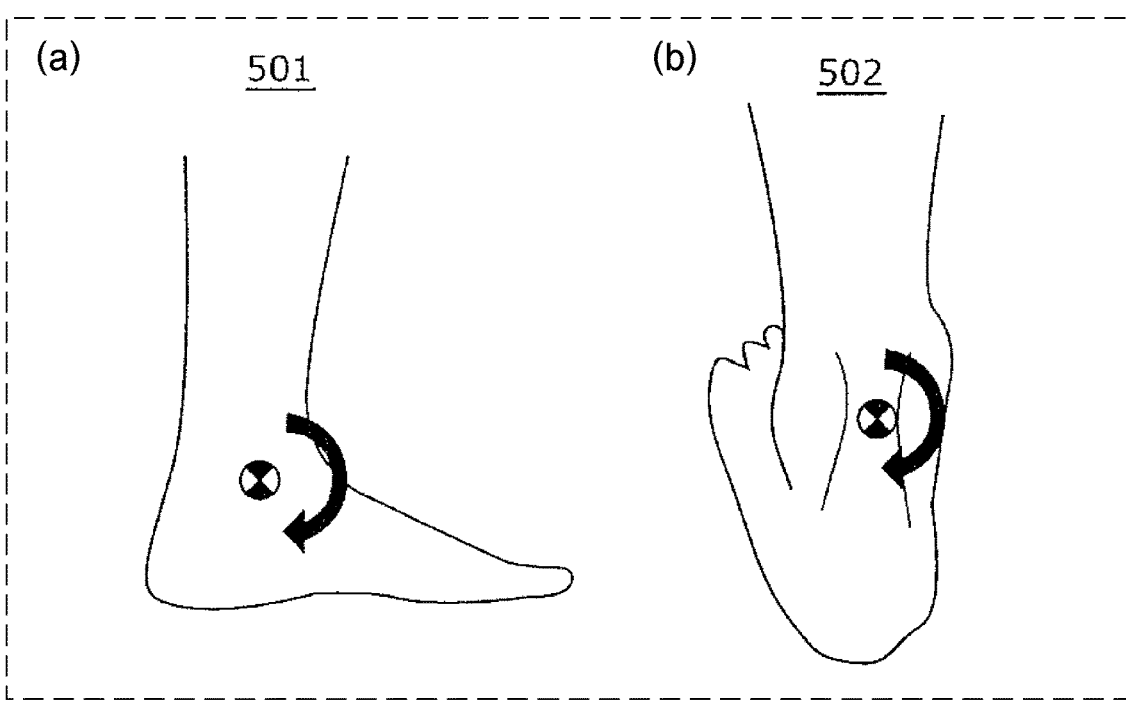
FIG. 5 illustrates a difference in walking style between subjects.

Therefore, a motor having one degree of freedom can perform assistance only in one direction, although walking differs between users. For example, assistance is performed in the direction in which the leg moves during walking, as indicated by an arrow on a leg 501 shown in part (a) of FIG. 5. However, it is difficult to apply a force in the outward direction of the ankle, as in the subject 402 illustrated in FIG. 4. Therefore, with a motor having one degree of freedom, it is difficult to assist a user in walking naturally.

The walking assistance apparatus 100 according to the first embodiment includes multiple wires, which are the first wire 104 and second wire 105, that are fixed to the heel of the user, and can change the tensions of the first wire 104 and the second wire 105. Therefore, for example, as in a leg 502 illustrated in part (b) of FIG. 5, the walking assistance apparatus 100 can generate a force in the adduction direction and the abduction direction or in the eversion direction and the inversion direction. Thus, it is possible to increase the degree of freedom in assistable direction and to perform assistance in natural walking in accordance with the walking style of the user.

The results of measuring the lengths of wires when the subject 401 and the subject 402 walked will be described. The wires were located inside and outside of a leg of each of the subjects A and B.

Figure 6:
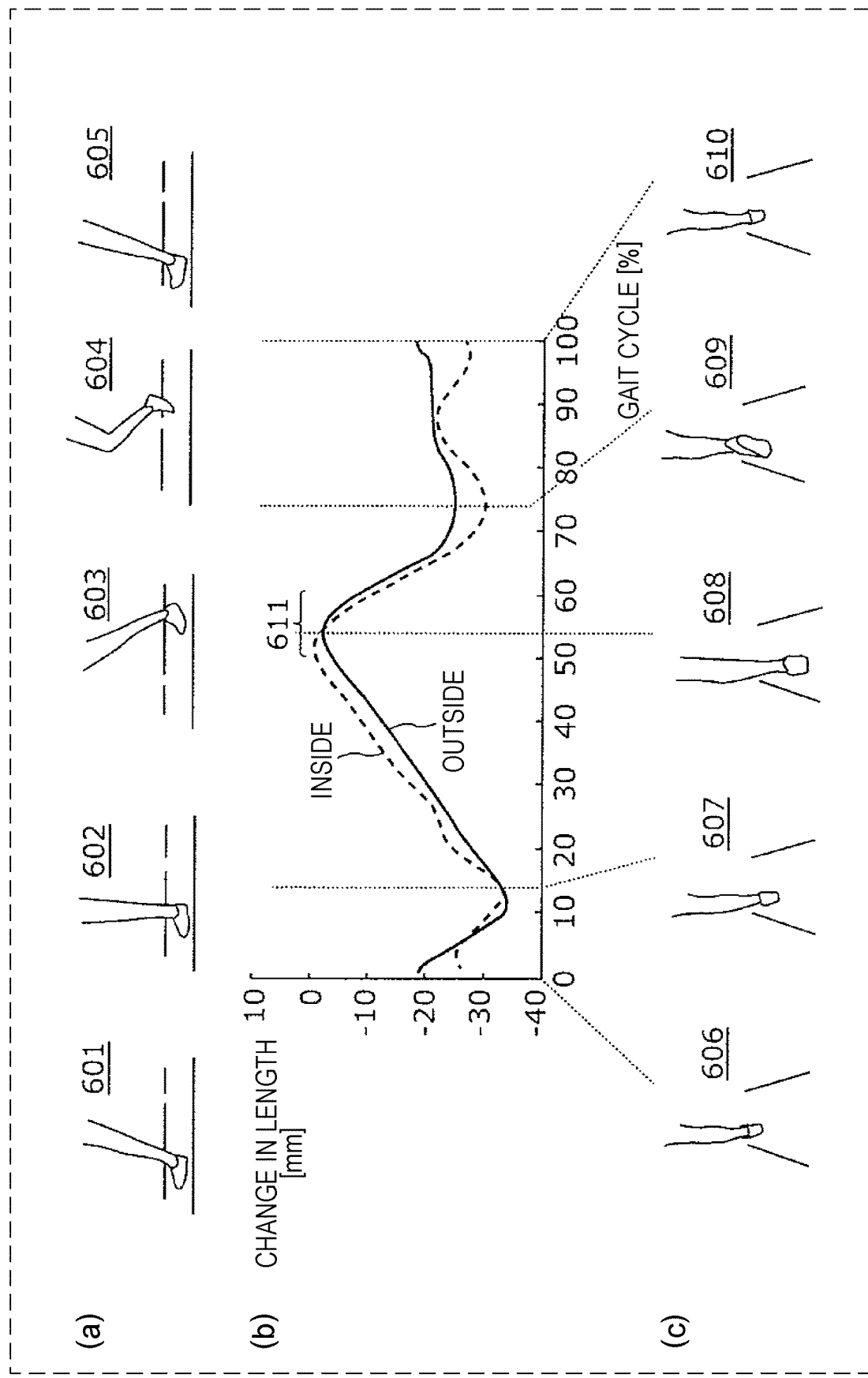
FIG. 6 illustrates changes in lengths of wires of a subject A.
Figure 7:
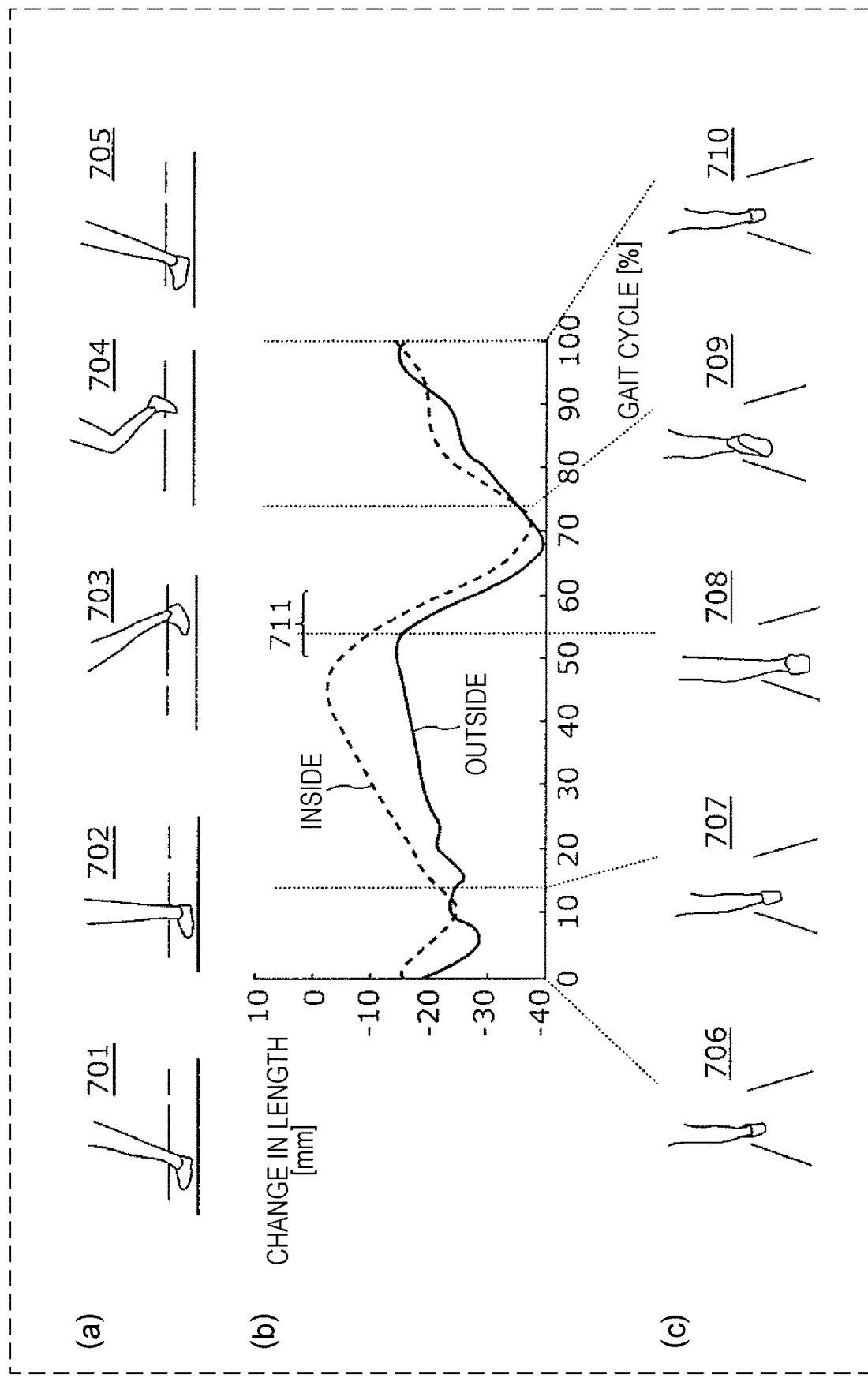
FIG. 7 illustrates changes in lengths of wires of a subject B.

FIG. 6 illustrates changes in lengths of the wires disposed inside and outside of the subject 401. FIG. 7 illustrates changes in lengths of the wires disposed inside and outside of the subject 402. In part (b) of FIG. 6 and part (b) of FIG. 7, the vertical axis represents the lengths (mm) of the wires, and the horizontal axis represents a gait cycle (%). FIGS. 6 and 7 each illustrate a gait cycle of the left foot.

When the ankle flexes (in a period 611 and a period 711), walking assistance was performed by winding the wires.

A change in length of a wire in the positive direction corresponds a motion in a direction such that the leg extends, and a change in length of wire in the negative direction corresponds to a motion in a direction such the leg contracts.

States 601 to 610 shown in FIG. 6 represent states when a user was walking. States 601 to 605 shown in part (a) of FIG. 6 are seen from a side of the user during walking. States 606 to 610 shown in part (c) of FIG. 6 are seen from the behind the user during walking. States 601, 602, 603, 604, and 605 respectively correspond to states 606, 607, 608, 609, and 610. The same applies to states 701 to 710 shown in FIG. 7.

Part (b) of FIG. 6 shows the lengths of the wires that were respectively disposed inside and outside of the subject 401, each of which was the average length for five cycles. Likewise, part (b) of FIG. 7 shows the lengths of the wires that were respectively disposed inside and outside of the subject 402, each of which was the average length of five cycles.

It can be seen from FIGS. 6 and 7 that the changes in lengths of the wires differ between the subjects. In particular, the changes in lengths in the period from state 607 to state 608 shown in in FIG. 6 considerably differ from the changes in lengths in the period from state 707 to state 708 shown in FIG. 7.

For the subject 401 shown in FIG. 6, in the period from state 607 to state 608, the change in length of the inside wire does not substantially differ from the change in length of the outside wire. On the other hand, in the period from state 707 to state 708 shown in FIG. 7, the change in length of the inside wire is smaller than the change in length of the outside wire.

In the period from state 607 to state 608, the change in length of the inside wire is smaller than the change in length of the outside wire. In the period from state 608 to state 609, the change in length of the inside wire is larger than the change in length of the outside wire.

For the subject 402 shown in FIG. 7, in substantially all periods, the change in length of the inside wire is smaller than the change in length of the outside wire.

As described above, it can be seen that change in distance from the ankle to the knee during walking differs between the subjects.

Motor Controller 208

Figure 8:
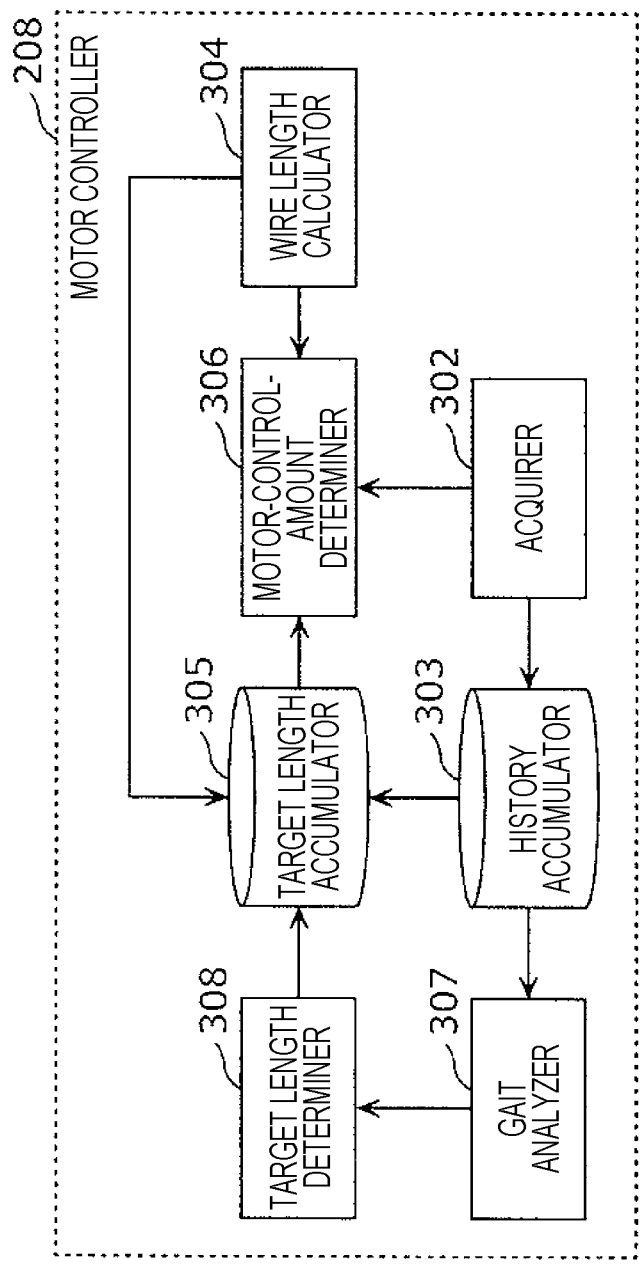
FIG. 8 is a functional block diagram of a motor controller.

FIG. 8 is a functional block diagram of the motor controller 208. The motor controller 208 illustrated in FIG. 8 includes an acquirer 302, a history accumulator 303, a wire length calculator 304, a target length accumulator 305, a motor-control-amount determiner 306, a gait analyzer 307, and a target length determiner 308.

Acquirer 302

The acquirer 302 acquires gait information of a user from the sensor 209. The gait information is information for calculating a gait cycle of the user.

An example of the sensor 209 is a foot switch sensor. The foot switch sensor is attached to a shoe sole. The foot switch sensor outputs an ON signal when the user is walking and the shoe sole is in contact with the ground, and outputs an OFF signal when the user is walking and the shoe sole is not in contact with the ground.

The acquirer 302 can acquire a state of the foot when the user is walking, in accordance with the signal output from the foot switch sensor.

Another example of the sensor 209 is an acceleration sensor. A state of the foot of the user during walking may be acquired based on information from the acceleration sensor. See, for example, p. 488, FIG. 1, p. 489, and FIG. 2 of IEEE TRANSACTIONS ON BIOMEDICAL ENGINEERING, VOL. 52, NO. 3, 2005.

Another example of the sensor 209 is an angle sensor. For example, the angle sensor is attached to a thigh of a user, and the acquirer 302 acquires the hip joint angle of the user as gait information. The gait analyzer 307 calculates a gait cycle based on change in cycle of the hip joint angle of the user.

History Accumulator 303

The history accumulator 303 accumulates gait information of a user acquired by the acquirer 302.

For example, the history accumulator 303 accumulates the present time in a gait cycle and a time when gait information is acquired, in association with each other. For example, the present time in the gait cycle is 0%.

FIG. 9 shows an example of gait information when the sensor 209 is a foot sensor. For example, the history accumulator 303 accumulates ON signals and OFF signals and times when the signals are acquired, in association with each other.

The gait information shown in FIG. 9 includes times when the sensor signal changes from an OFF signal to an ON signal (represented as sensor signal "ON") and times when the sensor signal changed from an ON signal to an OFF signal (represented as sensor signal "OFF").

Gait Analyzer 307

The gait analyzer 307 determines a period during which tensions are to be generated in the first wire 104 and the second wire 105 based on gait information of a user accumulated in the history accumulator 303.

First, the gait analyzer 307 acquires information on a gait cycle of a user based on the gait information of the user accumulated in the history accumulator 303.

The example of gait information shown in FIG. 9 includes data 1 (0 hours 10 minutes 3.143 seconds, ON), data 2 (0 hours 10 minutes 3.622 seconds, OFF), and data 3 (0 hours 10 minutes 3.952 seconds, ON).

For example, a cycle of one step of the user calculated based on data 1 to data 3 shown in FIG. 9 is 810 msec. Likewise, a cycle of one step of the user calculated based on data 3 to data 5 is 841 msec, a cycle of one step of the user calculated based on data 5 to data 7 is 809 msec, and a cycle of one step of the user calculated based on data 7 to data 9 is 786 msec.

Based on the information on the gait cycle, the gait analyzer 307 estimates the time of a predetermined period of a gait cycle in the next walking.

As the information on a gait cycle, for example, the average of gait cycles for predetermined number of steps is used. Even when a person looks like walking in the same way, the motion of a foot differs slightly between steps. It is possible to reduce an error in an individual user related to walking by using the average of gait cycles for a predetermined number of steps.

In the example shown in FIG. 9, the average time for the three steps is 820 msec ((810 msec+841 msec+809 msec)/3).

As an example, a case where the tensions of the first wire 104 and the second wire 105 are increased in the period from 50% to 60% of the gait cycle will be described.

In the next step, it can be estimated that, with respect to the time of data 7 when the fourth step is started, the period from 50% to 60% of the gait cycle is from 0 hours 10 minutes 6.012 seconds (5.602+(0.820×0.5)=6.012) to 0 hours 10 minutes 6.094 seconds (5.602+(0.820×0.6) =6.094). By generating tensions in the first wire 104 and the second wire 105 during this period, it is possible to assist the user in walking.

The gait analyzer 307 may determine whether the user is walking steadily. For example, if a predetermined number of gait cycles are within a predetermined time range, it is determined that the user is walking steadily. If it is determined that the user is walking steadily, the gait analyzer 307 estimates the time of a predetermined period in a gait cycle in the next walking by using the gait information.

For example, the gait analyzer 307 determines that the user is walking steadily if change in gait cycles for three steps (the difference between the maximum value and the minimum value of gait cycles for three steps) is within 100 msec. In the example shown in FIG. 9, the gait cycles for three steps is 810 msec, 841 msec, and 809 msec; and the change in gait cycle for three steps is 32 msec (841 msec− 809 msec); and therefore it is determined that the user is walking steadily.

Wire Length Calculator 304

The wire length calculator 304 calculates the lengths of the first wire 104 and the second wire 105 in order to apply predetermined tensions to the first wire 104 and the second wire 105 by using the motors 206 and 207.

For example, in order to prevent loosening of the first wire 104 and the second wire 105, predetermined tensions are constantly applied to the first wire 104 and the second wire 105 by using the motors 206 and 207. Thus, the wire length calculator 304 can calculate the lengths of the first wire 104 and the second wire 105 based on the winding amounts of the first wire 104 and the second wire 105. The lengths of the first wire 104 and the second wire 105 are the lengths thereof between the heel fastener 103 and the knee fastener 102.

For example, when the user is standing, the wire length calculator 304 causes a user to set the first wire 104 and the second wire 105 so that the first wire 104 and the second wire 105 are not loose.

For example, when a user wears the heel fastener 103 and the knee fastener 102, the wire length calculator 304 causes the user to wear the first wire 104 and the second wire 105 so that the first wire 104 and the second wire 105 are not loose.

The wire length calculator 304 may acquire information on loosening of the first wire 104 and the second wire 105 from sensors for detecting loosening of the first wire 104 and the second wire 105.

Loosening of the first wire 104 may be detected by measuring a change in driving electric current of the motor 206 when the motor 206 winds the first wire 104. The driving electric current of the motor 206 is proportional to the torque, that is, proportional to the tension generated in the wire.

An increase in the driving electric current of the motor 206 when the motor 206 winds the first wire 104 indicates that the tension of the first wire 104 is increasing, that is, that the first wire 104 is not loose. On the other hand, no change in the driving electric current of the motor 206 when the motor 206 winds the first wire 104 indicates that the tension of the first wire 104 does not change, that is, that the first wire 104 is loose.

A decrease in the driving electric current of the motor 206 when the motor 206 unwinds the first wire 104 indicates that the tension of the first wire 104 is decreasing, that is, that the first wire 104 has changed from a tight state to a loose state. In other words, it is detected that the first wire 104 was not loose before the motor 206 unwinds the first wire 104. On the other hand, no change in the driving electric current of the motor 206 when the motor 206 unwinds the first wire 104 indicates that the tension of the first wire 104 continues to be low, that is, that the first wire 104 continues to be loose. In other words, it is detected that the first wire 104 was loose before the motor 206 unwinds the first wire 104.

Detection of loosening of the wire 105 by using the motor 207 can be explained in the same way as the above-described detection of loosening of the wire 104 by using the motor 206.

Loosening of the first wire 104 and the second wire 105 may be detected by detecting the tensions of the first wire 104 and the second wire 105 by using force sensors 2101 and 2102.

If the information on loosening of the wires indicates that the first wire 104 or the second wire 105 is loose, for example, an alarm may be output from an external output unit to prompt a user to tighten the first wire 104 or the second wire 105. An example of the external output unit is a speaker or a display.

In a state in which the wires are not loose, the wire length calculator 304 controls the motors 206 and 207 to generate a tension of, for example, 1 N to 2 N in each of the first wire 104 and the second wire 105. As a result, in a state in which loosening of the first wire 104 and the second wire 105 is prevented while a user walks straight, the wire length calculator 304 acquires information on the lengths of the first wire 104 and the second wire 105. To be specific, the wire length calculator 304 calculates the lengths of the first wire 104 and the second wire 105 based on the winding amounts of the first wire 104 and the second wire 105.

Target Length Determiner 308

The target length determiner 308 determines the target lengths of the first wire 104 and the second wire 105 based on a predetermined criterion and the lengths of the first wire 104 and the second wire 105 in a gait cycle.

The distance between the heel and the knee when a user is walking without assistance, as illustrated in FIGS. 6 and 7, is used. To be more specific, the distances between the heel and the knee where the first wire 104 is disposed and the distance between the heel and the knee where the second wire 105 is disposed are used.

The target length determiner 308 sets the target lengths of the first wire 104 and the second wire 105 based on the measured distances and a predetermined criterion, and accumulates the target values in the target length accumulator 305. The measured distances are the distance between the heel and the knee where the first wire 104 is disposed and the distance between the heel and the knee where the second wire 105 is disposed when the user is walking without assistance.

The predetermined criterion is (a) to maintain the relationship between the distance between the heel and the knee where the first wire 104 is disposed when assistance is not performed and the distance between the heel and the knee where the second wire 105 is disposed when assistance is not performed, and, (b) in a predetermined period in a gait cycle, to reduce the distance between the heel and the knee where the first wire 104 is disposed and the distance between the heel and the knee where the second wire 105 is disposed.

To be more specific, if the first wire 104 is longer than the second wire 105 when the motors 206 and 207 are not driven and a user is walking, the motors 206 and 207 are controlled to make the first wire 104 longer than the second wire 105. If the first wire 104 is shorter than the second wire 105 when the motors 206 and 207 are not driven and a user is walking, the motors 206 and 207 are controlled to make the first wire 104 shorter than the second wire 105. Thus, it is possible to appropriately assist a user in walking in accordance with the walking style of the user.

The distance between the heel and the knee where the first wire 104 is disposed when assistance is not performed is also referred to as a first distance. The distance between the heel and the knee where the second wire 105 is disposed when assistance is not performed is also referred to as a second distance.

For example, for the users in the examples shown in FIGS. 6 and 7, if the first distance is smaller than the second distance, the target length of the first wire 104 is smaller than the target length of the second wire 105.

The target length determiner 308 may determine the target lengths for the entirety of the gait cycle or may determine the target lengths for a part of the gait cycle.

Figure 10A:
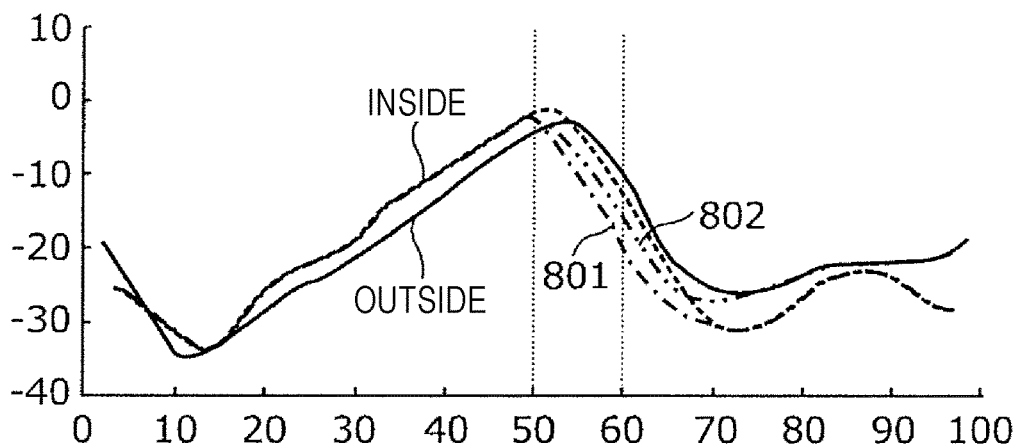
FIG. 10A illustrates target paths of wire length control.

FIG. 10A illustrates specific examples of the target lengths of the first wire 104 and the second wire 105.

The target lengths shown in FIG. 10A are lengths in a period of 50% or more and 60% or less of a gait cycle. Examples of the target length includes a target length 801 of the first wire 104, which is shown by an alternate long and short dash line, and a target length 802 of the second wire 105, which is shown by a two-dot chain line.

Figure 10B:
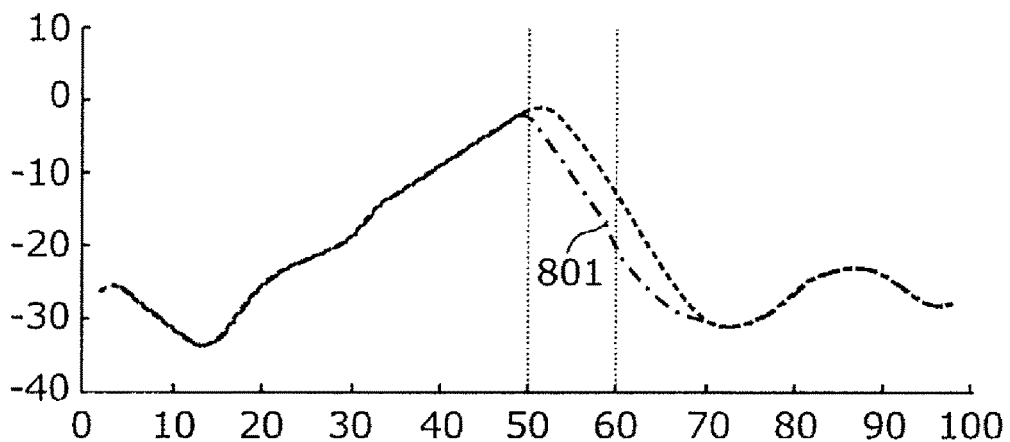
FIG. 10B illustrates target paths of wire length control.
Figure 10C:
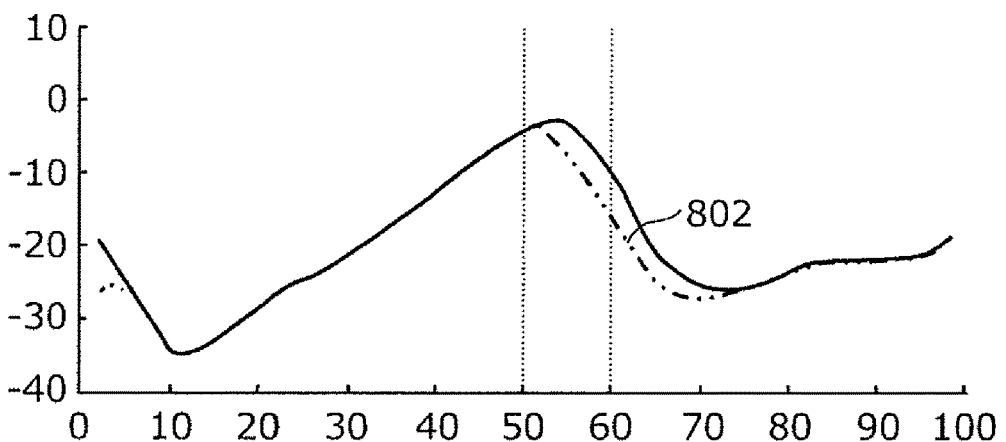
FIG. 10C illustrates target paths of wire length control.

In the period of 50% or more and 60% or less of the gait cycle shown in FIG. 10A, the target lengths 801 and 802 are shorter by 10 mm to 20 mm than the lengths of the first wire 104 and the second wire 105 when assistance is not performed. In the period of 50% or more and 60% of the gait cycle or less shown in FIG. 10A, the target lengths 801 and 802 may be shorter by a predetermined rate (for example, 5%) than the lengths of the first wire 104 and the second wire 105 when assistance is not performed. FIG. 10B shows the target length of the first wire 104 in FIG. 10A, and FIG. 10C shows the target length of the second wire 105 in FIG. 10A.

When the walking assistance apparatus 100 performs assistance based on the target lengths, compared with usual walking, the degree of flexion of the ankle increases, and a force with which the foot strikes the ground increases during walking. As a result, it is possible to increase the stride of the user and to increase the walking speed.

For a user whose stride is larger than a predetermined value and whose ankle flexion is larger than a predetermined level, the target length determiner 308 may set target lengths of the wires that are shorter than predetermined lengths. A user whose ankle flexion is large is a user who causes large changes in lengths of the wires.

If it is desirable to increase the assistance effect, the target length determiner 308 may set the target lengths of the wires shorter. On the other hand, for a user that does not need a large assistance amount, the target length determiner 308 may set target lengths that are longer than the predetermined lengths by 5 mm to 10 mm.

Target Length Accumulator 305

The target length accumulator 305 accumulates the target lengths determined by the target length determiner 308. To be specific, the target length accumulator 305 accumulates the target rotation amounts of the motors 206 and 207 corresponding to the lengths of the first wire 104 and the second wire 105 to be wound.

Motor-Control-Amount Determiner 306

The motor-control-amount determiner 306 refers to the target lengths in the target length accumulator 305, and, based on the lengths of the first wire 104 and the second wire 105 calculated by the wire length calculator 304, determines voltages for controlling the motors 206 and 207.

To be specific, in the period from 50% to 60% of the gait cycle, if the lengths calculated by the wire length calculator 304 are larger than the target lengths in the target length accumulator 305, the motor-control-amount determiner 306 performs control in order to reduce the lengths of the wires by applying voltages to the motors 206 and 207 to increase the winding amounts of the wires.

In this way, the motor controller 208 controls the winding amounts of the first wire 104 and the second wire 105 by using the motor 206 and the motor 207. In accordance with the differences between first criteria that specify the length of the first wire 104 and the length of the second wire 105 for each gait cycle and the winding amounts of the first wire 104 and the second wire 105, the motor controller 208 controls the motor 206 to reduce the length of the first wire 104 and the motor 207 to reduce the length of the second wire 105 in a predetermined period of a gait cycle in the next walking of the user. Therefore, it is possible to assist the user in walking with an appropriate rotation amount of the ankle.

Moreover, the motor-control-amount determiner 306 may perform feedback control on the target lengths based on the lengths of the first wire 104 and the second wire 105 calculated by the wire length calculator 304.

With the operations described above, it is possible to assist a user in walking in accordance with the walking style of the user by winding the first wire 104 and the second wire 105 with the motors 206 and 207 at a ground strike timing in the period of 50% to 60% of the gait cycle.

Flowchart of Walking Assistance Apparatus 100

Figure 11:
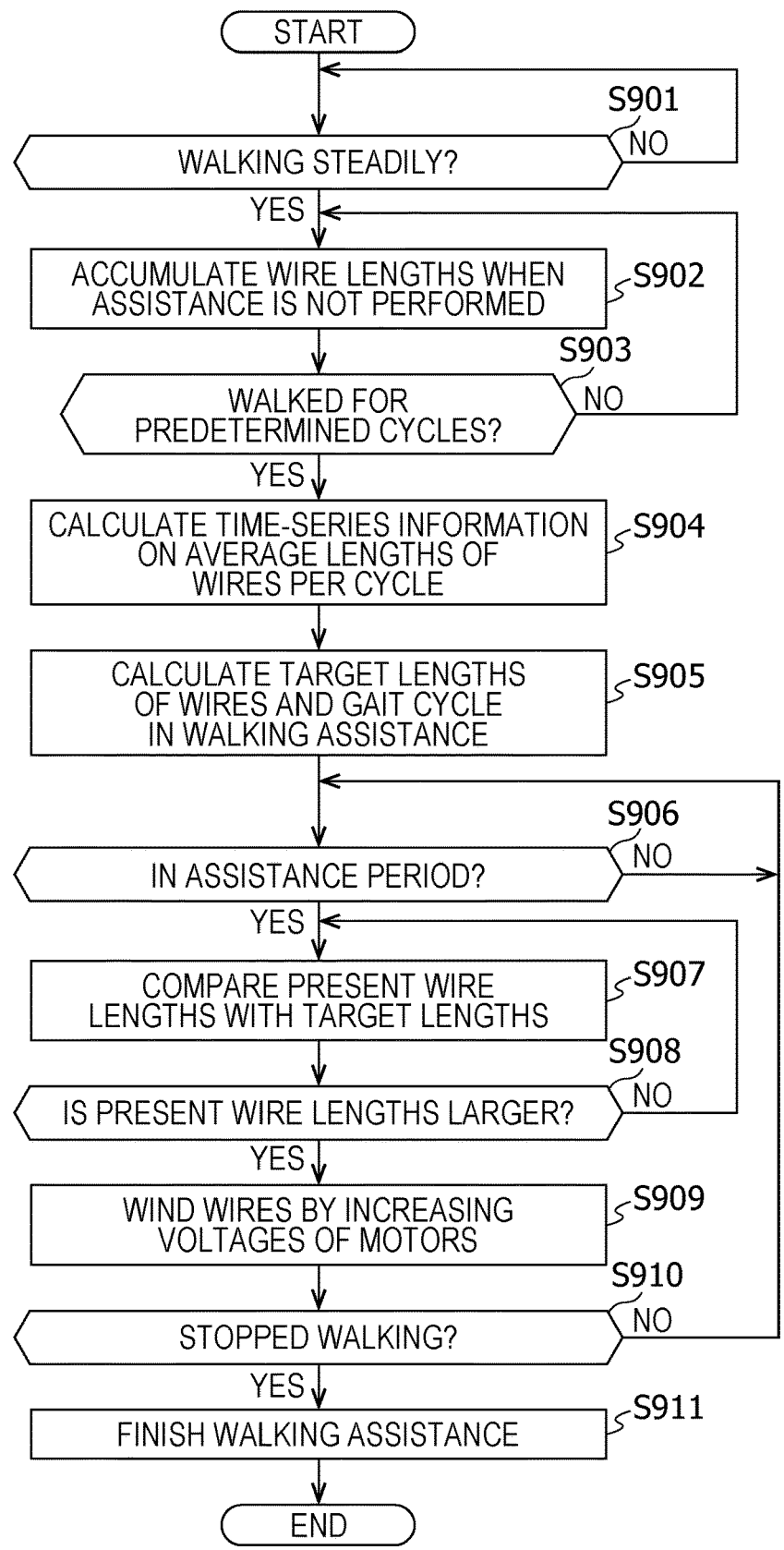
FIG. 11 is a flowchart of the first embodiment.

Referring to FIG. 11, which is a flowchart of control performed by the motor controller 208, the operations of the walking assistance apparatus 100 will be described.

Step S901

The gait analyzer 307 acquires gait information of a user. Based on the gait information, the gait analyzer 307 determines whether the user is walking steadily. For example, the gait analyzer 307 determines that the user is walking steadily if the times of gait cycles of the user are regular intervals.

If the user is not walking steadily, the gait analyzer 307 repeats step 901. If the user is walking steadily, the process proceeds to step S902.

Step S902

The wire length calculator 304 calculates the lengths of the first wire 104 and the second wire 105 when walking assistance is not performed. The wire length calculator 304 may store the lengths of the first wire 104 and the second wire 105 in a memory in association with the time when the lengths are measured.

The wire length calculator 304 may acquire precalculated lengths of the first wire 104 and the second wire 105 when walking assistance is not performed.

Step S903

The gait analyzer 307 determines whether the user has walked for predetermined cycles. For example, if the user has walked for three cycles, the process proceeds to step S905. If the user has not walked for predetermined cycles, the process returns to step S902.

Step S904

The wire length calculator 304 calculates the lengths of the first wire 104 and the second wire 105. For example, the wire length calculator 304 calculates the average of the length of the first wire 104 and the average of the length of the second wire 105 for three cycles of walking. Thus, the graph of the wire lengths during walking, which is shown in FIG. 6, is created.

Step S905

The target length determiner 308 determines the target length of the first wire 104 and the target length of the second wire 105 based on the predetermined criterion and the lengths of the first wire 104 and the second wire 105 when walking assistance is not performed. As a result, for example, the target length determiner 308 creates the target paths of the wire lengths shown in FIGS. 10A to 10C. The target paths are examples of a target value. The target paths are accumulated in the target length accumulator 305.

Step S906

Based on the gait cycle estimated by the gait analyzer 307, the motor-control-amount determiner 306 determines whether the present time is a timing at which assistance control is to be performed. For example, if the present time is 50% or more and 60% or less of the gait cycle, walking assistance is performed by generating tensions. As the information on the gait cycle, the gait information acquired by the gait analyzer 307, which is shown in FIG. 9, is used.

Step S907

The wire length calculator 304 acquires the length of the first wire 104 and the length of the second wire 105 at present. The motor-control-amount determiner 306 compares the target lengths accumulated in the target length accumulator 305 with the calculated present lengths of the first wire 104 and the second wire 105.

Step S908

If the present lengths of the first wire 104 and the second wire 105 are respectively longer than the target values, the process proceeds to step S909. If the present lengths of the first wire 104 and the second wire 105 are respectively shorter than target values, the process returns to step S907.

Step S909

The motor-control-amount determiner 306 determines the driving voltages of the motors 206 and 207 for adjusting the lengths of the first wire 104 and the second wire 105 to the target lengths, and sends control signals to the motors 206 and 207. For example, the motor-control-amount determiner 306 determines the voltages with reference to a criterion including voltage values corresponding to the differences between the lengths of the first wire 104 and the second wire 105 and the target lengths.

Step S910

The motor-control-amount determiner 306 determines whether the user has stopped walking; and, if the user has stopped walking, finishes the process. If the user is walking, the process returns to step S906.

If the gait analyzer 307 acquires information that the user is not walking steadily, the motor-control-amount determiner 306 determines that the user has stopped walking.

With the operations described above, the wire lengths are controlled in accordance with a walking state of the user, and it is possible to assist the user in walking at an appropriate timing during walking.

Advantages

The walking assistance apparatus 100 according to the present embodiment can assist a user in walking by using the first wire 104 and the second wire 105, which are disposed on the left side and the right side of a leg of the user. Thus, the walking assistance apparatus 100 can generate torques for assistance in a direction in which the ankle of the user is flexed and in a direction in which the ankle is abducted. Therefore, it is possible to realize natural assistance by generating tensions while adjusting the lengths of the wires in accordance with the motion of the ankle in the walking style of the user.

First Modification of First Embodiment

In the walking assistance apparatus 100 according to the first embodiment, the elongation of the first wire 104 may be larger than the elongation of the second wire 105. The elongation of the first wire 104 can be represented as a length by which the first wire 104 elongates when a tension is applied to the first wire 104 by a motor. For example, the first wire 104 elongates by 1% of the entire length of the first wire 104 when a force of 15 kN is applied. A force more than 15 kN may be required to elongate the first wire 104 by 1%.

As illustrated in FIGS. 6 and 7, the change in length of the first wire 104, which is disposed inside, is larger than that of the second wire 105, which is disposed outside, and a load tends to be applied to the first wire 104. Therefore, it is possible to effectively reduce breakage of the first wire 104 by making the elongation of the first wire 104 larger than that of the second wire 105. Moreover, it is possible to reduce the cost of the second wire 105, because the elongation of the second wire 105 is smaller than the elongation of the first wire 104.

Second Modification of First Embodiment

In the walking assistance apparatus 100 according to the first embodiment or the first modification of the first embodiment, the maximum speed of the first wire 104 may be higher than the maximum speed of the second wire 105.

The maximum speed of a wire is the maximum value of the speed with which the wire is wound by a motor corresponding to the wire. For example, the maximum speed of a wire is 0.35 m/s.

As illustrated in FIGS. 6 and 7, the change in length of the first wire 104, which is disposed inside, is larger than that of the second wire 105, which is disposed outside. Therefore, it is possible to increase the response speed of assisting in adduction of the ankle of the user by making the maximum speed of the first wire 104 higher than that of the second wire 105. Thus, it is possible to effectively assist the user in walking.

Third Modification of First Embodiment

In the walking assistance apparatus 100 according to the first embodiment or the first or second modification of the first embodiment, the maximum torque of the motor 206 may be larger than the maximum torque of the motor 207.

As illustrated in FIGS. 6 and 7, the change in length of the first wire 104, which is disposed inside, is larger than that of the second wire 105, which is disposed outside, and a load tends to be applied to the first wire 104. Therefore, the tension applied to the first wire 104 can be easily made larger than the tension applied to the second wire 105 by making the maximum torque of the motor 206, which is connected to the first wire 104, be larger than that of the motor 207. Moreover, it is possible to reduce the cost of the motor 207, because the maximum torque of the motor 207 is smaller than the maximum torque of the motor 206.

Fourth Modification of First Embodiment

Figure 12:
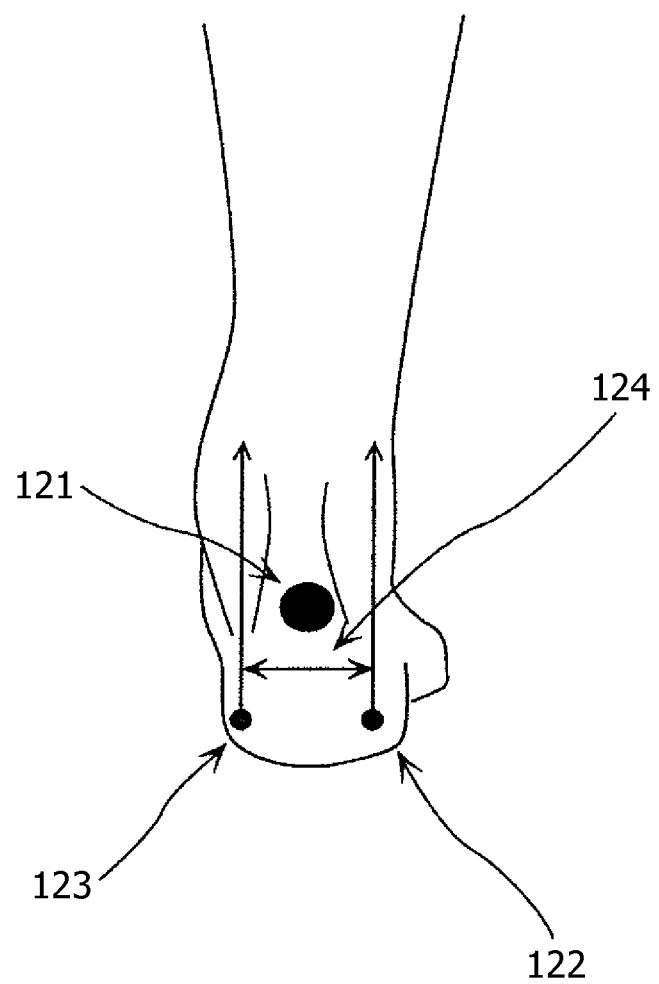
FIG. 12 illustrates wire attachment positions on a heel fastener.

In the walking assistance apparatus 100 according to the first embodiment or any of the first to third modifications of the first embodiment, as illustrated in FIG. 12, the distance 124 between the fixing position where the first wire 104 is fixed and the fixing position where the second wire 105 is fixed may 20 mm or more.

FIG. 12 is a rear view of the left foot of a user.

In this way, the heel fasteners 103a and 103b are respectively connected to a fixing position 122 where the first wire 104 is fixed and a fixing position 123 where the second wire 105 is fixed, with the center of gravity 121 of the heel therebetween. Thus, as in the leg 502 shown in part (b) of FIG. 5, it is possible to effectively generate a force having a moment inclined in the leftward or rightward inclination.

Second Embodiment

In the walking assistance apparatus 100 according to the first embodiment, as shown in the external views of FIGS. 1A and 1B, the first wire 104 and the second wire 105 do not intersect each other and are fixed in an approximately parallel shape.

In a walking assistance apparatus 200 according to the second embodiment, the arrangement of a first wire 104A and a second wire 105A differ from the arrangement of the first wire 104 and the second wire 105 of the walking assistance apparatus 100, in order to assist a user in walking straight and to increase the effect in assisting the user in walking to change direction leftward or rightward.

In order to generate a moment in the leftward or rightward rotation direction by using the first wire 104A and the second wire 105A, the first wire 104A and the second wire 105A may be worn by a user in such a way that tensions can be generated in diagonal directions. As illustrated in FIG. 13, one end of the first wire 104A is connected to the right side of the heel, and a portion of the first wire 104A between the one end and the other end is connected to the left side of the knee. That is, the first wire 104A is connected to a left-half region of the knee fastener 102. A position on the knee fastener 102 to which the first wire 104A is connected is also referred to as a third position.

As illustrated in FIG. 13, one end of the second wire 105A is connected to the left side of the heel, and a portion of the second wire 105A between the one end and the other end is connected to the right side of the knee. That is, the second wire 105A is connected to a right-half region of the knee fastener 102. A position on the knee fastener 102 to which the second wire 105A is connected is also referred to as a forth position.

Thus, it is possible to generate a moment in the leftward or rightward rotation direction.

This will be described with reference to FIG. 14. Part (a-1) of FIG. 14 is a rear view of a foot when wires are arranged parallel to each other (parallel type). Part (a-2) of FIG. 14 is a top view of the foot when the wires are arranged parallel to each other (parallel type). Part (b-1) of FIG. 14 is a rear view of a foot when wires are arranged to cross each other (cross type). Part (b-2) of FIG. 14 is a top view of the foot when the wires are arranged to cross each other (cross type).

In the parallel-type wire arrangement, as illustrated in part (a-1) of FIG. 14, the wires extend in the up-down direction, and the tensions of the wires are generated in the up-down direction. Therefore, as illustrated in part (a-2) of FIG. 14, when seen from above, a moment in a rotation direction generated in the foot of the user is substantially zero.

In contrast, in the cross-type wire arrangement, as illustrated in part (b-1) of FIG. 14, the wires extend in directions that are inclined leftward and rightward at small angles relative to the up-down direction, and the tensions of the wires are generated in the inclined directions. As a result, in addition to a force in the up-down direction, forces in the leftward and rightward directions are generated. That is, with the cross-type wire arrangement, as illustrated in part (b-2) of FIG. 14, it is possible to generate a moment in a rotation direction around the center of gravity of the foot. In contrast to the wires in the parallel-type wire arrangement, which cannot assist in a motion in the rotation direction, the wires in the cross-type wire arrangement can perform assistance with the moment in the rotation direction.

The functional block diagram of the walking assistance apparatus 200 according to the second embodiment is the same as that of the walking assistance apparatus 100 according to the first embodiment. As with the walking assistance apparatus 100, the walking assistance apparatus 200 can assist a user in walking by controlling the lengths of the first wire 104A and the second wire 105A.

The walking assistance apparatus 200 according to the second embodiment can assist a user in walking by controlling the tensions of the first wire 104A and the second wire 105A. The method will be described below.

Figure 15A:
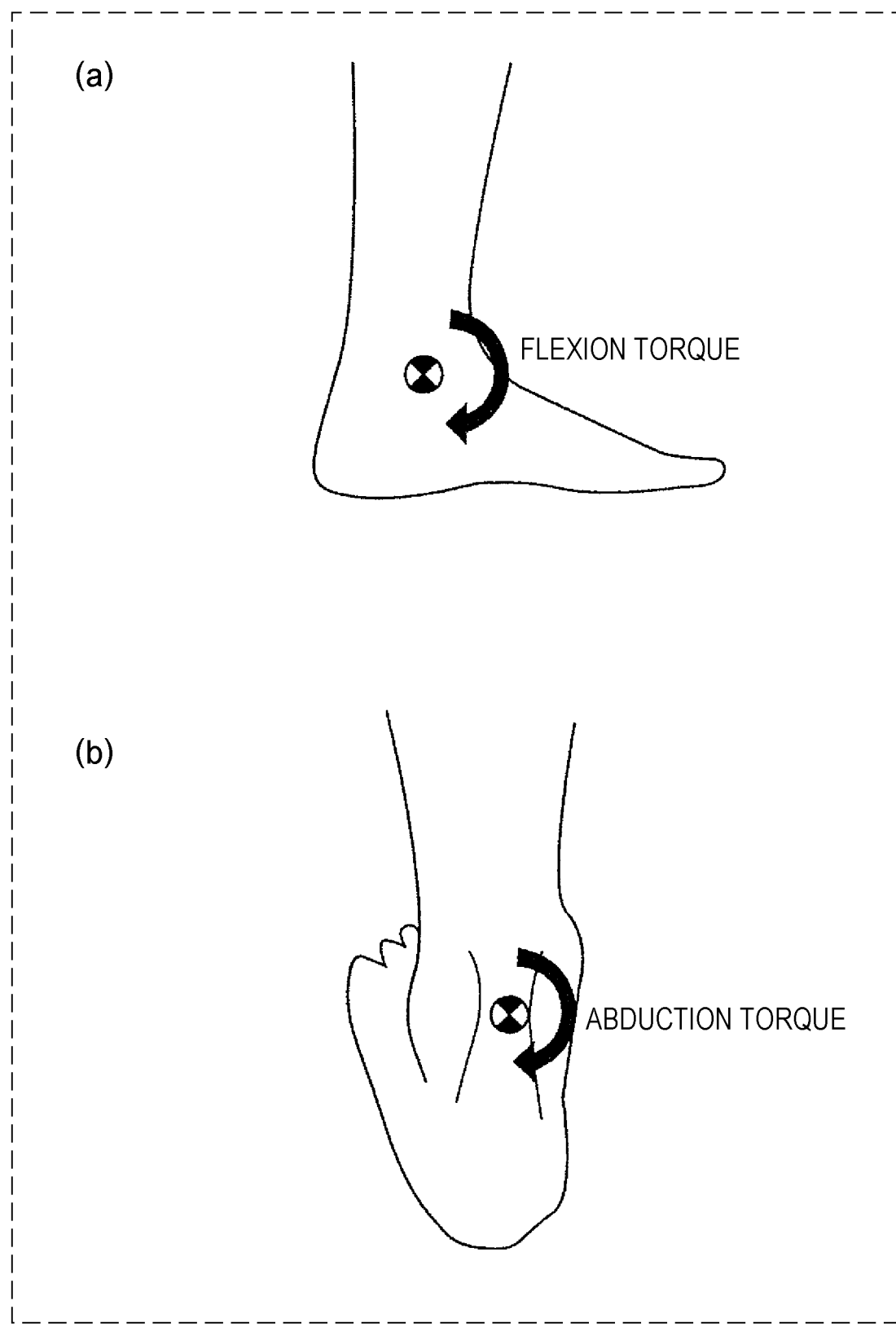
FIG. 15A illustrates a torque pattern during straight walking.

Parts (a) and (b) of FIG. 15A respectively illustrate a flexion torque and an abduction torque when a user is walking straight. Parts (a), (b), and (c) of FIG. 15B are graphs respectively representing the flexion torque, the abduction torque, and the changes in tensions of the first wire 104A and the second wire 105A in a gait cycle when a user is walking straight.

It is assumed that the straight walking of the user is ideal walking with no inclination of the foot. Therefore, the abduction torque is not generated. Assistance is performed by using the first wire 104A and the second wire 105A in such a way that a torque that is 20% of a torque generated by the user is generated.

Figure 15B:
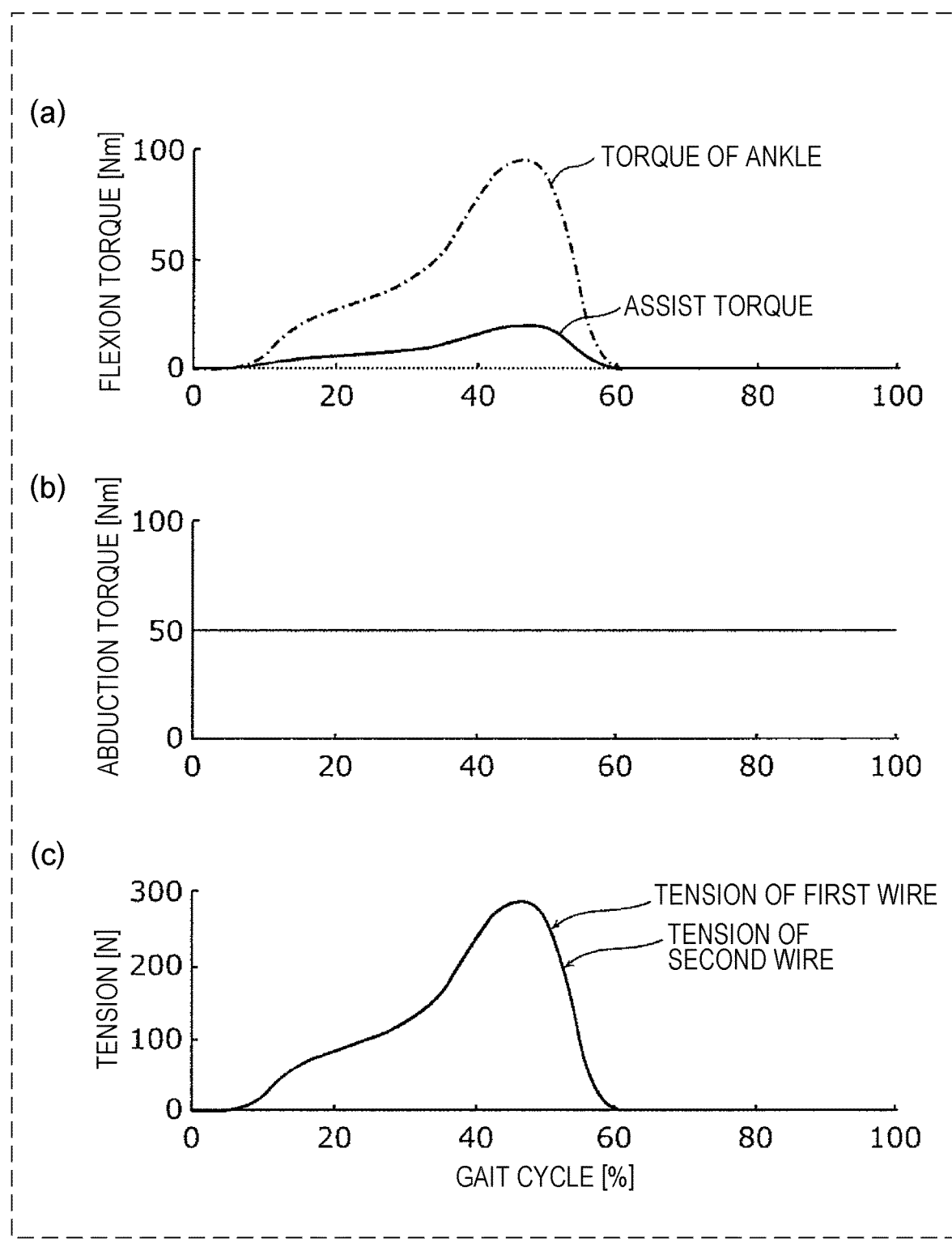
FIG. 15B illustrates a torque pattern during straight walking.

The tensions of the first wire 104A and the second wire 105A can be represented by a pattern shown in Part (c) of FIG. 15B. In this pattern, the tensions of the first wire 104A and the second wire 105A are the same. However, as in the case of the subject 402 shown in part (b) of FIG. 4, whose ankle is flexed, an abduction angle is generated, and the assistance torques generated in the first wire 104A and the second wire 105A differ from each other.

That is, if the change in length of the first wire 104A and the change in length of the second wire 105A are the same, the same tensions are generated in the first wire 104A and the second wire 105A.

If the change in length of the first wire 104A and the change in length of the second wire 105A differ from each other, a tension generated in one of the first wire 104A and the second wire 105A, whose length becomes shorter, is made larger.

A motor controller 208A of the walking assistance apparatus 200 according to the second embodiment controls the motor 206 and the motor 207 in accordance with the tensions applied to the first wire 104A and the second wire 105A.

Figure 16:
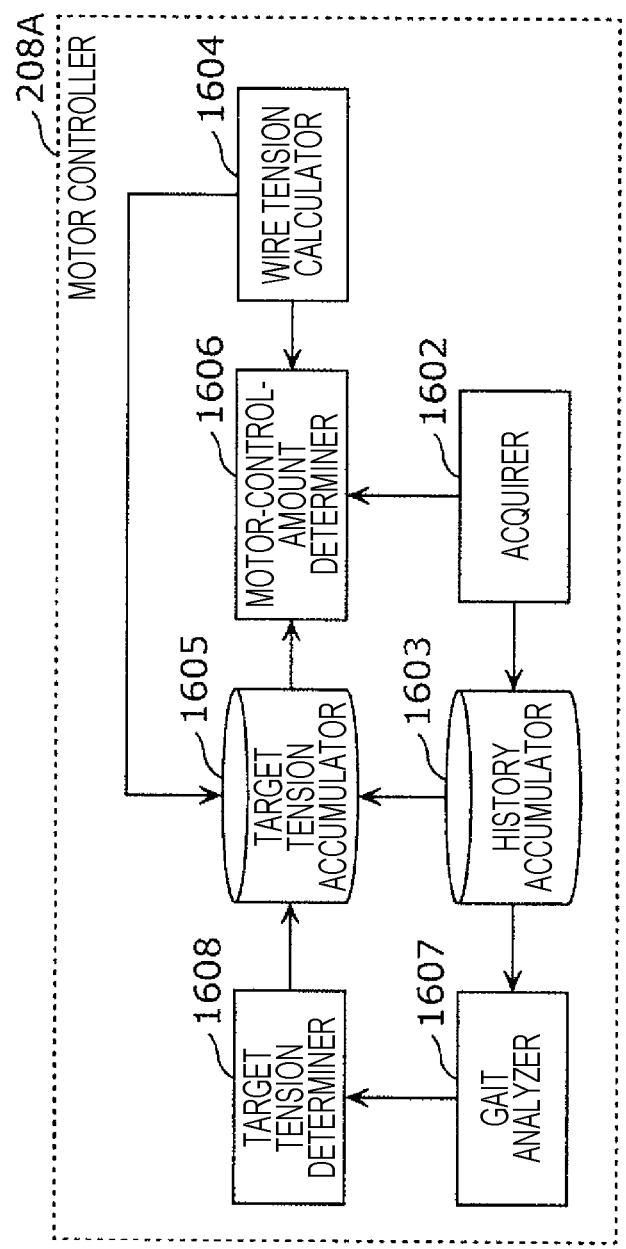
FIG. 16 is a functional block diagram of a motor controller.

FIG. 16 is a functional block diagram of the motor controller 208A. The motor controller 208A illustrated in FIG. 16 includes an acquirer 1602, a history accumulator 1603, a wire tension calculator 1604, a target tension accumulator 1605, a motor-control-amount determiner 1606, a gait analyzer 1607, and a target tension determiner 1608.

Operations of these components will be described. Descriptions of the acquirer 1602, the history accumulator 1603, and the gait analyzer 1607, which are respectively the same as the acquirer 302, the history accumulator 303, and the gait analyzer 307, will be omitted.

The target tension accumulator 1605 accumulates the target pattern of the tensions of the first wire 104 and the second wire 105 illustrated in part (c) of FIG. 15B.

Wire Tension Calculator 1604

The wire tension calculator 1604 acquires, from the motors 206 and 207, voltages applied to the motors 206 and 207 and electric currents of the motors 206 and 207 at that time. The wire tension calculator 1604 calculates tensions applied to the first wire 104A and the second wire 105A by using the voltages applied to the motors 206 and 207 and the electric currents of the motors 206 and 207.

Motor-Control-Amount Determiner 1606

The motor-control-amount determiner 1606 determines voltages to be applied to the motors 206 and 207 by using the target pattern of tensions accumulated in the target tension accumulator 1605 and the tensions of the first wire 104A and the second wire 105A calculated by the wire tension calculator 1604.

In this way, the motor controller 208A acquires the tensions of the first wire 104A and the second wire 105A, and, in accordance with the differences between second criteria that specify the tension of the first wire 104A and the tension of the second wire 105A for each gait cycle and the tensions of the first wire 104A and the second wire 105A, the motor controller 208A controls the motor 206 to reduce the length of the first wire 104A and the motor 207 to reduce the length of the second wire 105A in a predetermined period of a gait cycle in the next walking of the user. Therefore, it is possible to assist the user in walking with an appropriate force.

Figure 17:
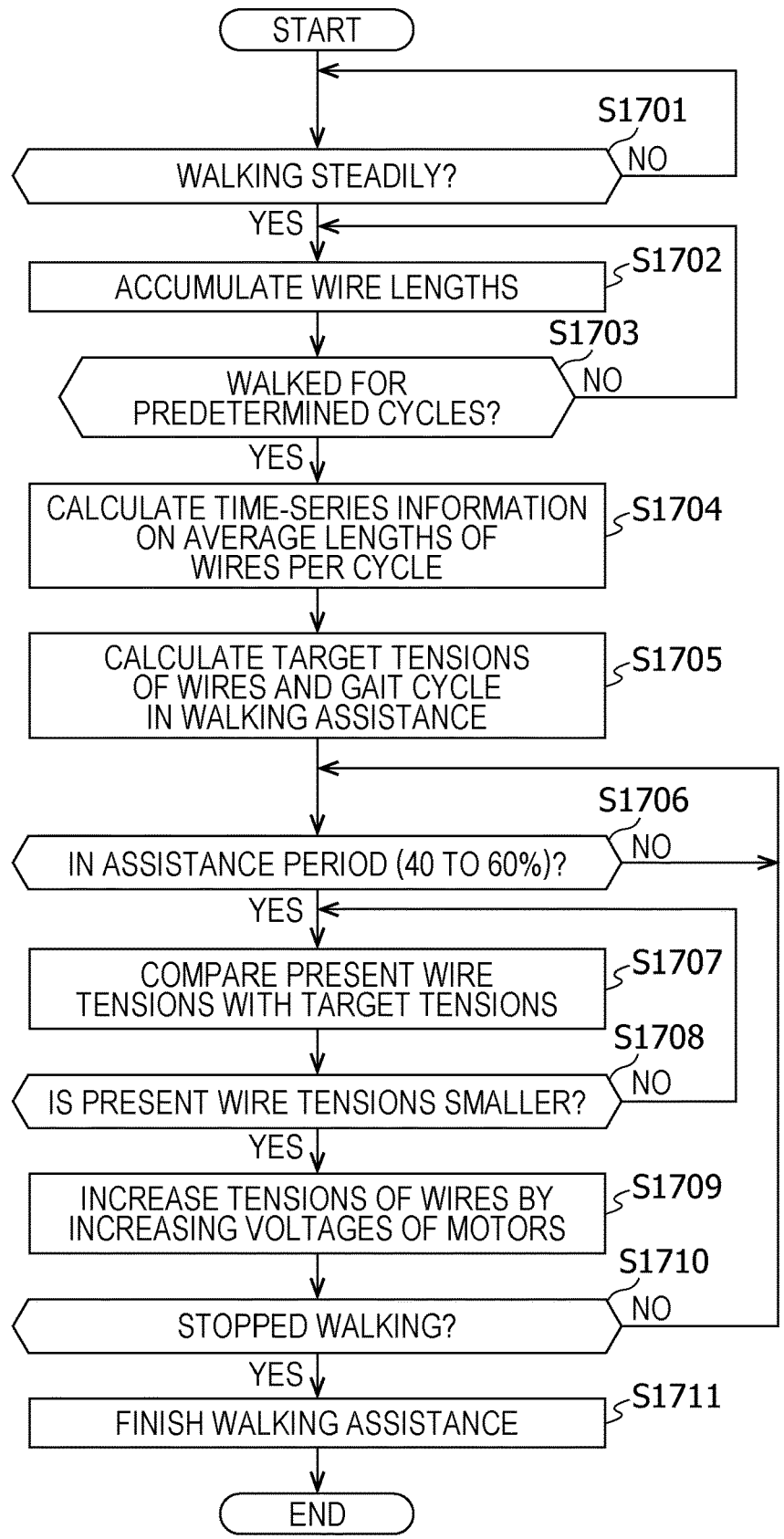
FIG. 17 is a flowchart of the second embodiment.

FIG. 17 is a flowchart of the operations of the walking assistance apparatus 200, which controls the motors by using tensions.

Descriptions of steps S1701 to S1706, in which operations the same those of steps S901 to S906 in the first embodiment are performed, will be omitted. In the present embodiment, the target tensions of the wires are calculated, instead of the target lengths of the wires calculated in the first embodiment.

Step S1707

The wire tension calculator 1604 compares the present tensions of the first wire 104A and the second wire 105A with the target tensions.

Step S1708

If the present tensions of the wires are smaller, the process proceeds to the next step. If the present tensions of the wires are larger, the process returns to step S1707.

Step S1709

The motor-control-amount determiner 306 determines the voltages of the motors 206 and 207 for increasing the tensions of the first wire 104A and the second wire 105A to the target tensions. To be specific, the motor-control-amount determiner 306 increases the voltages of the motors 206 and 207 in accordance with the differences between the target tensions of the first wire 104A and the second wire 105A.

Step S1710

The motor-control-amount determiner 1606 determines whether the user has stopped walking. If the user has stopped walking, the process returns to step S1706.

By performing the operations described above, it is possible to assist the user in walking by controlling the tensions.

First Modification of Second Embodiment

In the second embodiment, assistance in straight walking of a user has been described. However, when assisting a user in walking to change direction leftward or rightward, it is effective to control the tensions of the left and right wires differently. A walking assistance apparatus 300 according to the present modification differs from the walking assistance apparatus 200 according to the second embodiment in that the motor controller 208A is replaced with a motor controller 208B and that the walking assistance apparatus 300 further includes a rotation detector 1909.

Figure 18:
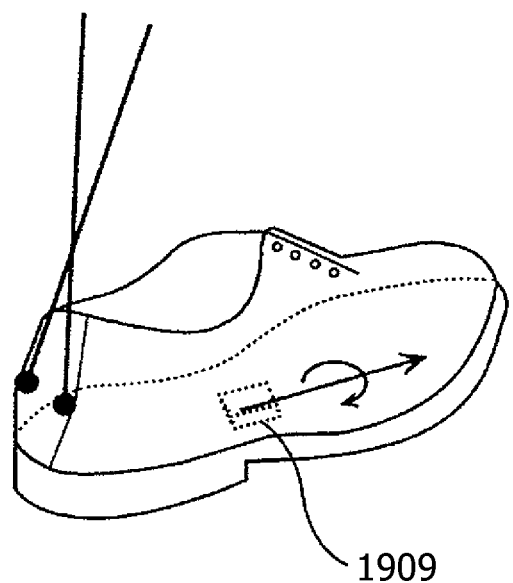
FIG. 18 illustrates a position where a sensor for detecting a turning direction is attached.

As illustrated in FIG. 18, the walking assistance apparatus 300 further includes the rotation detector 1909 and detects a change in the direction of the user by using the rotation detector 1909.

The rotation detector 1909 detects a rotation when a user changes direction leftward or rightward. An example of the rotation detector 1909 is a gyro sensor. The gyro sensor is attached to a shoe sole or to the heel fastener 103.

For example, the gyro sensor detects the inclination of the heel fastener 103. If the gyro sensor detects the inclination, the motor controller 208B determines that the user is walking in the leftward or rightward direction.

Figure 19:
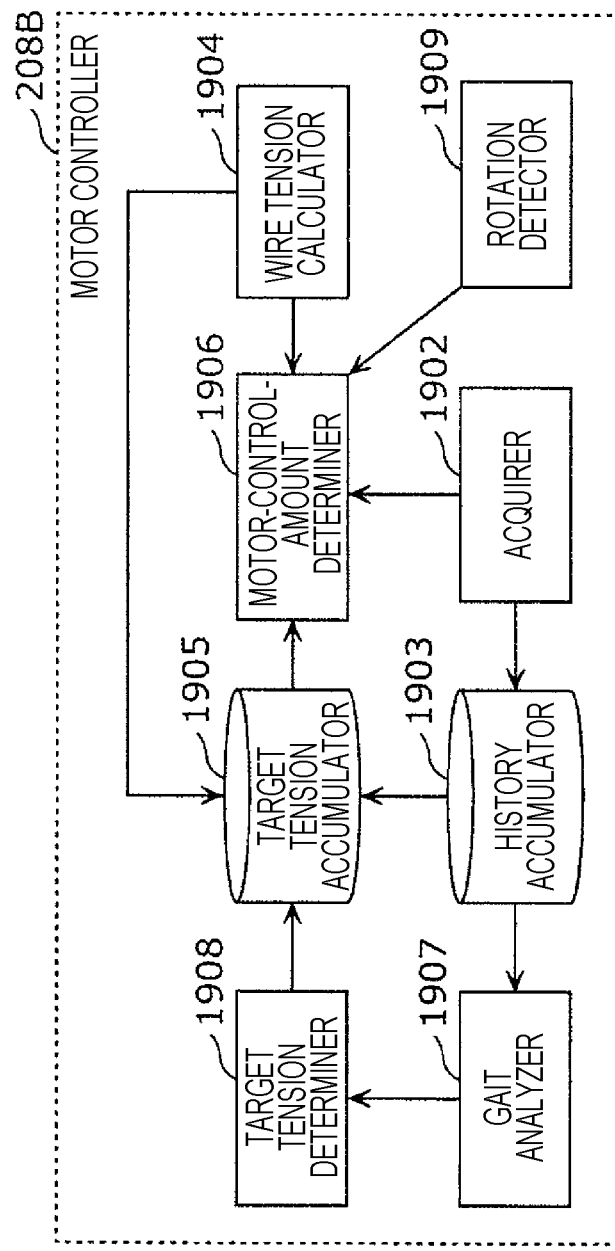
FIG. 19 is a functional block diagram of a motor controller.

FIG. 19 is a functional block diagram of the motor controller 208B. As illustrated in FIG. 19, the motor controller 208B includes an acquirer 1902, a history accumulator 1903, a wire tension calculator 1904, a target tension accumulator 1905, a motor-control-amount determiner 1906, a gait analyzer 1907, and the rotation detector 1909.

Descriptions of the acquirer 1902, the history accumulator 1903, the wire tension calculator 1904, the target tension accumulator 1905, the motor-control-amount determiner 1906, and the gait analyzer 1907, which are respectively the same as the acquirer 1602, the history accumulator 1603, the wire tension calculator 1604, the target tension accumulator 1605, the motor-control-amount determiner 1606, and the gait analyzer 1607, will be omitted. The motor controller 208B, which is similar to the motor controller 208A, further includes the rotation detector 1909. When the rotation detector 1909 detects a change in the direction of a user, the motor controller 208B changes the pattern of controlling the motors 206 and 207.

Figure 20A:
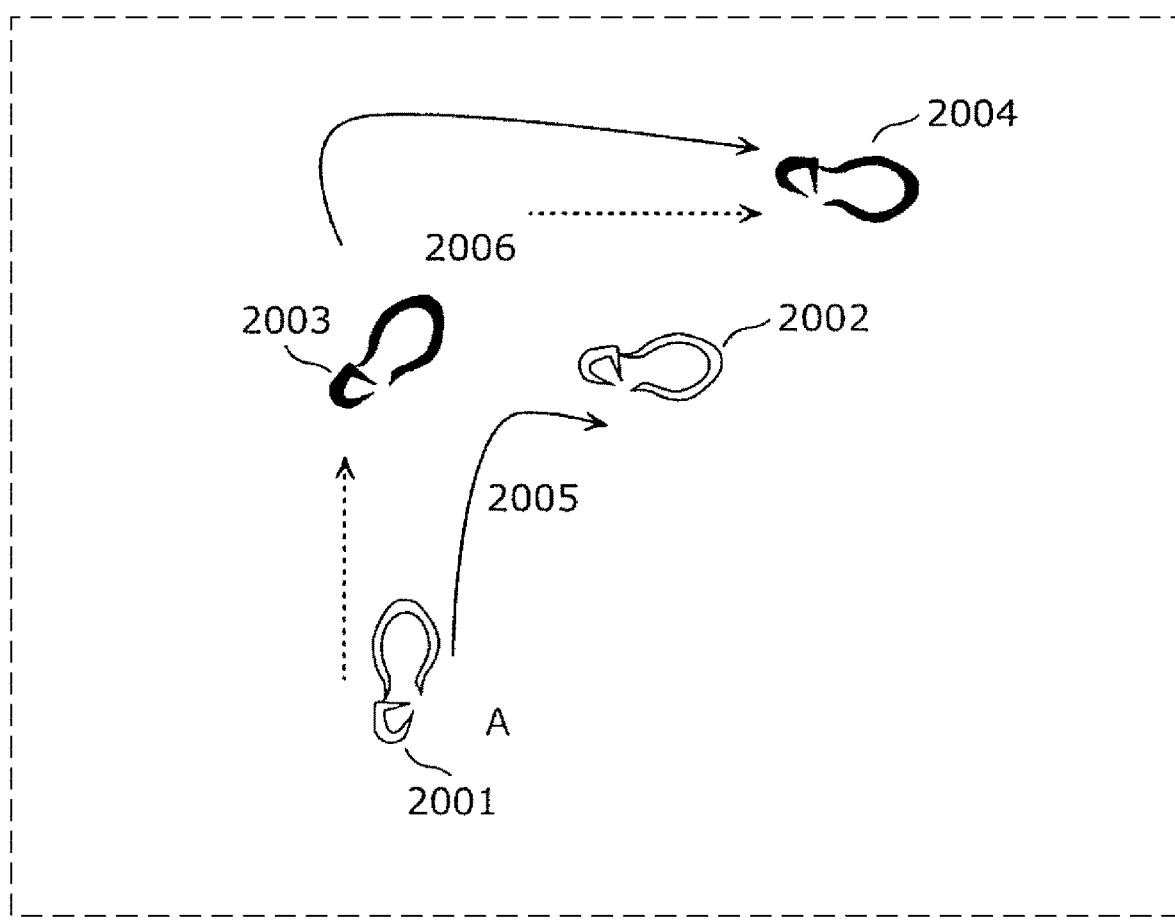
FIG. 20A illustrates a torque pattern when changing direction.

This control pattern will be described further in detail. FIG. 20A illustrates a state in which a user walking on a right foot 2001, a left foot 2003, a right foot 2002, and a left foot 2004 in this order.

When the user turns rightward from the position of the left foot 2003, the user walks on the right foot 2002 and then on the left foot 2004. At this time, the right foot requires a force for turning rightward as indicated by an arrow 2005, and the left foot requires a force for turning rightward as indicated by an arrow 2006.

Figure 20B:
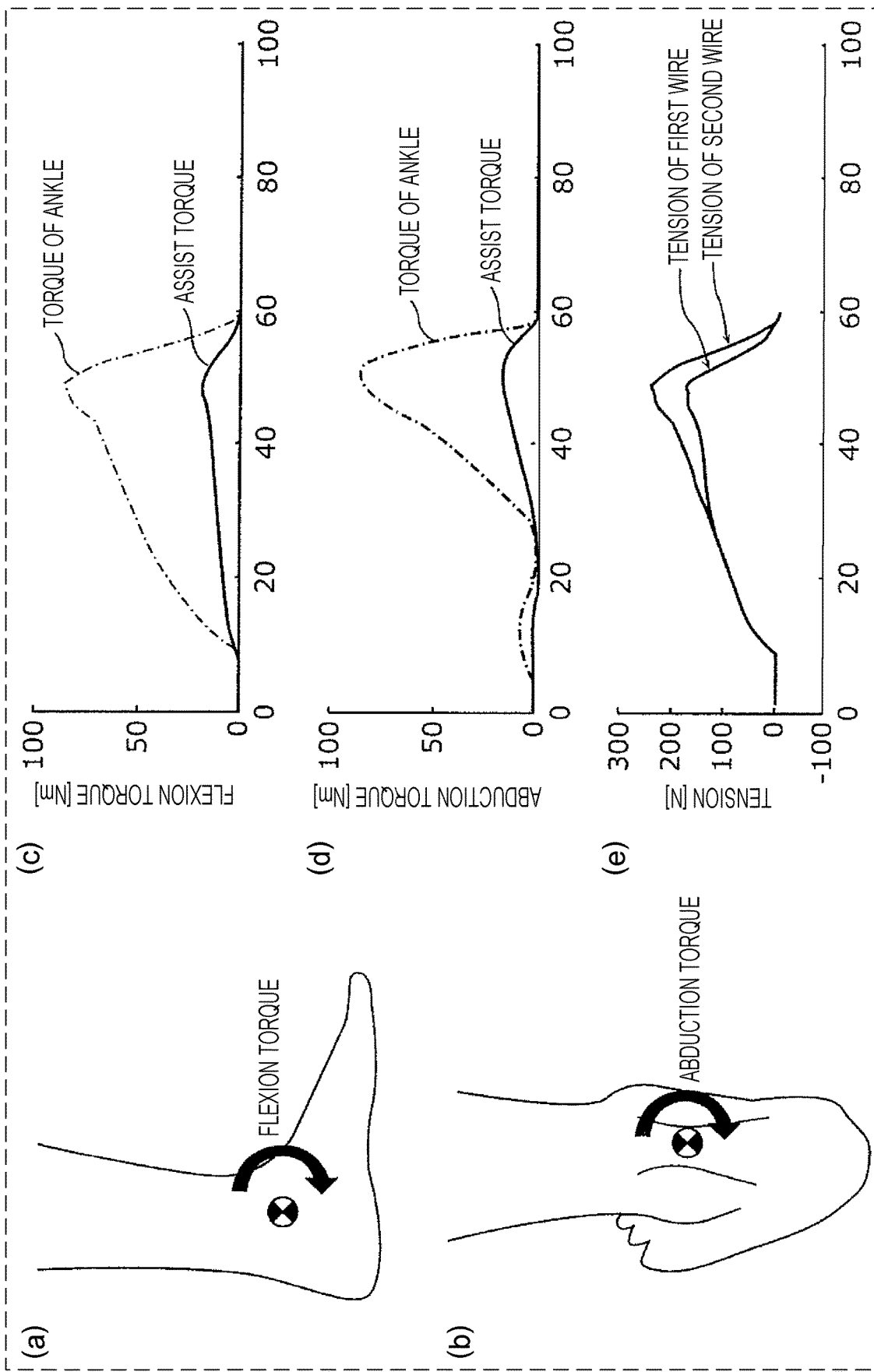
FIG. 20B illustrates a torque pattern when changing direction.

Parts (a) and (b) of FIG. 20B respectively illustrate a flexion torque and an abduction torque of the user. Parts (c), (d), and (e) of FIG. 20B are graphs respectively representing the flexion torque, the abduction torque, and the changes in tensions of the first wire 104A and the second wire 105A in a gait cycle when a user changes direction rightward. As illustrated in part (d) of FIG. 20B, when the user changes direction rightward, the abduction torque is generated, in contrast to Fig. part (b) of 15B, which corresponds to straight walking.

Accordingly, as illustrated in part (e) of FIG. 20B, a difference occurs between the tensions of the first wire 104A and the second wire 105A. The target tension accumulator 1905 accumulates target tension patterns in which the tension differs between the left and right wires. For example, in a target tension pattern for a right turn, the tension of the second wire 105 is larger than the tension of the first wire 104. In a target tension pattern for a left turn, the tension of the second wire 105 is smaller than the tension of the first wire 104.

When a change in the direction of the user leftward or rightward is detected, a predetermined target tension pattern is selected and control is performed. That is, if the rotation detector 1909 detects a change in direction rightward, the motor controller 208B selects a target tension pattern for a right turn, which is accumulated in the target tension accumulator 1905, and controls the motors 206 and 207 by using the target tension pattern for the right turn. If the rotation detector 1909 detects a change in direction leftward, the motor controller 208B selects a target tension pattern for a left turn, which is accumulated in the target tension accumulator 1905, and controls the motors 206 and 207 by using the target tension pattern for the left turn.

In this way, based on turning direction and gait information of the user, the motor controller 208B controls the motor 206 to reduce the length of the first wire 104A and the motor 207 to reduce the length of the second wire 105A at a predetermined timing. Therefore, it is possible to appropriately assist the user in walking even when the user changes direction rightward or leftward during walking.

In the second embodiment, the wire tension calculator 1604 estimates the tensions of the first wire 104A and the second wire 105A by using the electric currents of the motors. However, as illustrated in part (b) of FIG. 21, force sensors 2101 and 2102 may be disposed on the first wire 104A and the second wire 105A, and the tensions of the first wire 104A and the second wire 105A may be measured by using the force sensors 2101 and 2102. The voltages of the motors 206 and 207 may be determined by calculating the differences between the target tensions and the tensions of the first wire 104 and the second wire 105 measured by the force sensors.

In the first embodiment, the motors 206 and 207 are controlled based on the lengths of the first wire 104 and the second wire 105. However, this is not a limitation. As in the second embodiment, the motors 206 and 207 may be controlled based on the tensions of the first wire 104 and the second wire 105. In this case, as with part (b) of FIG. 21, as illustrated in part (a) of FIG. 21, the force sensors 2101 and 2102 may be disposed on the first wire 104 and the second wire 105 of the walking assistance apparatus 100 according to the first embodiment, and the tensions of the first wire 104 and the second wire 105 may be measured by using the force sensors 2101 and 2102.

In the second embodiment, the motors 206 and 207 are controlled based on the tensions applied to the first wire 104A and the second wire 105A. However, this is not a limitation. As in the first embodiment, the motors 206 and 207 may be controlled based on the lengths of the first wire 104 and the second wire 105.

Figure 22:
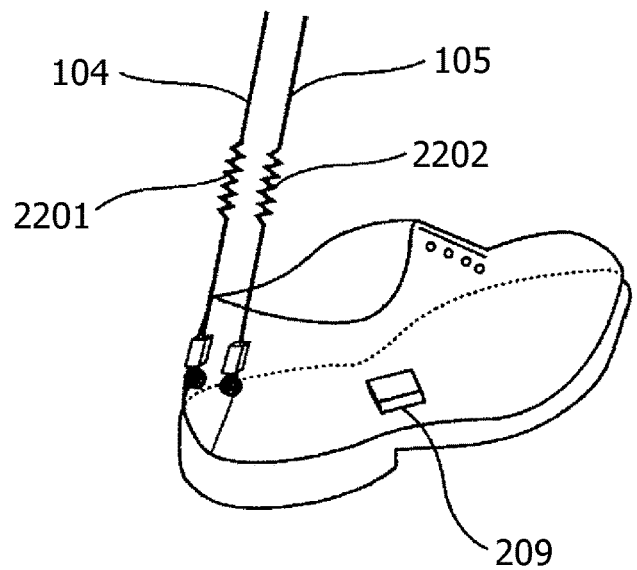
FIG. 22 is an external view when springs are attached.

In the first and second embodiments, the first wire 104 and the second wire 105 are directly fixed to the heel fastener 103. However, as illustrated in FIG. 22, springs 2201 and 2202 may be respectively disposed between the first wire 104 and the heel fastener 103 and between the second wire 105 and the heel fastener 103. That is, the first wire 104 and the second wire 105 may be fixed to the heel fastener 103 via the springs 2201 and 2202. In this case, it is possible to perform control with rigidity.

Figure 23:
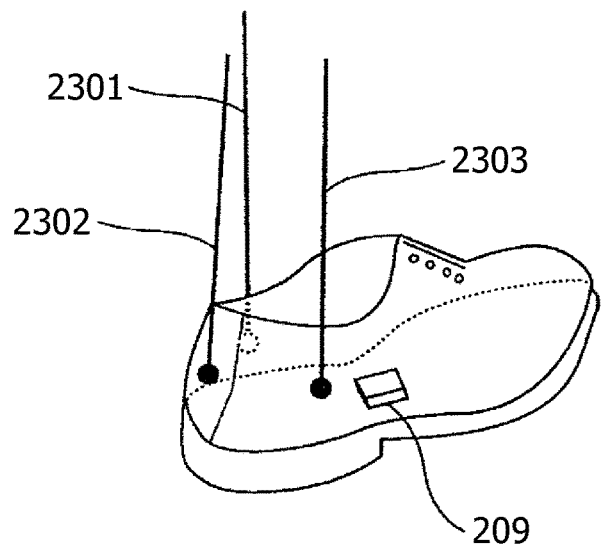
FIG. 23 is an external view illustrating assistance using three wires.

The walking assistance apparatuses 100, 200, and 300 according to the first and second embodiments perform assistance in walking by using two wires. As illustrated in FIG. 23, assistance may be performed by using three wires 2301, 2302, and 2303. In this case, it is possible to increase the degree of freedom in controlling an abduction torque while increasing a flexion torque during walking. In this case, the three wires 2301, 2302, and 2303 are respectively connected to three motors (not shown).

Figure 24:
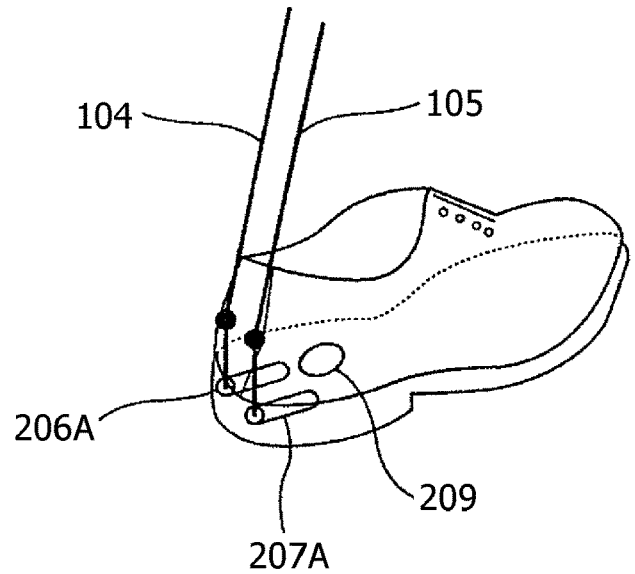
FIG. 24 is an external view when a motor is disposed in a heel.

In the walking assistance apparatuses 100, 200, and 300 according to the first and second embodiments, the motors 206 and 207 are attached to the knee belt 101. However, as illustrated in FIG. 24, motors 206A and 207A, which are respectively fixed to the first wire 104 and the second wire 105, may be attached to the heel of a shoe, the inside of a shoe, or the heel fastener 103.

In the present disclosure, all or some of units and devices or all or some of the functional blocks shown in each of the block diagrams of FIGS. 2, 8, 16, and 19 may be implemented in one electric circuit or one or more electronic circuits each including a semiconductor apparatus, a semiconductor integrated circuit (IC), or a large scale integration (LSI). The LSI or the IC may be integrated into one chip or may be a combination of multiple chips. For example, a functional block other than a storage device may be integrated into one chip. A device that is called as an LSI or an IC may be called, depending on the degree of integration, a system LSI, a very large scale integration (VLSI), or an ultra large scale integration (ULSI). A field programmable gate array (FPGA), which is an LSI that is programmable after having been produced, and a reconfigurable logic device, which allows reconstruction of the connection relationship of the inside of the LSI or setting up of circuit segments inside the LSI, may be used for the same purpose.

The functions or the operations of all or some of the units and the devices may be performed by software processing. In this case, the software is recorded a non-transitory storage medium including one or more ROMs, an optical disc, or a hard disk drive. When the software is executed by a processor, the software causes the processor and peripheral devices to perform specific functions coded in the software. The systems or devices may include one or at least one non-transitory storages medium in which a software is recorded, a processor, and a hardware device that is necessary, such as an interface.

A walking assistance apparatus according to the present disclosure can be used to assist a user in walking or in performing a walking motion.

What is claimed is:

1. A walking assistance apparatus comprising:
a knee fastener to be worn on a knee of a leg of a user;
a heel fastener to be worn on a heel of the leg of the user;
a first wire connected to the knee fastener and the heel fastener and to be located on a back side of the user;
a second wire connected to the knee fastener and the heel fastener and to be located on the back side of the user;
a first motor connected to the first wire;
a second motor connected to the second wire; and
a control circuit that controls the first motor and the second motor, wherein
the first wire is connected to a first position included in a right-half region of the heel fastener,
the second wire is connected to a second position included in a left-half region of the heel fastener, and
the control circuit acquires gait information of the user, and, based on the gait information, the control circuit controls the first motor to reduce a length of the first wire and the second motor to reduce a length of the second wire at a predetermined timing.

2. The walking assistance apparatus according to claim 1, wherein
the gait information of the user includes information on a gait cycle of the user, and
the control circuit controls the first motor to reduce the length of the first wire and the second motor to reduce the length of the second wire in a period of 40% or more and 60% or less of the gait cycle of the user as the predetermined timing,
where a percentage of the gait cycle is defined such that a time when a foot of the user contacts a ground is 0% and a time when the foot of the user contacts the ground next time is 100%.

3. The walking assistance apparatus according to claim 1, wherein
the first wire is disposed on an inside of the leg,
the second wire is disposed on an outside of the leg, and
an elongation of the first wire is larger than an elongation of the second wire.

4. The walking assistance apparatus according to claim 1, wherein
the first wire is disposed on an inside of the leg,
the second wire is disposed on an outside of the leg, and
a maximum torque of the first motor is larger than a maximum torque of the second motor.

5. The walking assistance apparatus according to claim 1, wherein
the first wire is disposed on an inside of the leg,
the second wire is disposed on an outside of the leg, and
a maximum speed of the first wire is higher than a maximum speed of the second wire.

6. The walking assistance apparatus according to claim 1, wherein
a distance between the first position and the second position is 20 mm or larger.

7. The walking assistance apparatus according to claim 1, wherein
the first wire is connected to a third position included in a left-half region of the knee fastener, and
the second wire is connected to a fourth position included in a right-half region of the knee fastener.

8. The walking assistance apparatus according to claim 1, wherein
the control circuit further acquires information on a gait cycle of the user by using the gait information, and
by using the information on the gait cycle, the control circuit controls the first motor to reduce the length of the first wire and the second motor to reduce the length of the second wire in a predetermined period of a gait cycle in a next walking of the user.

9. The walking assistance apparatus according to claim 1, wherein
the control circuit further acquires winding amounts of the first wire and the second wire by using the first motor and the second motor, and
in accordance with differences between first criteria that specify a length of the first wire and a length of the second wire for each gait cycle and the winding amounts of the first wire and the second wire, the control circuit controls the first motor to reduce the length of the first wire and the second motor to reduce the length of the second wire in a predetermined period of a gait cycle in a next walking of the user.

10. The walking assistance apparatus according to claim 1, further comprising:
   a first spring disposed between the first wire and the heel fastener; and
   a second spring disposed between the second wire and the heel fastener.

11. The walking assistance apparatus according to claim 1, wherein
   the control circuit acquires tensions of the first wire and the second wire, and
   in accordance with differences between second criteria that specify a tension of the first wire and a tension of the second wire for each gait cycle and the tensions of the first wire and the second wire, the control circuit controls the first motor to reduce the length of the first wire and the second motor to reduce the length of the second wire in a predetermined period of a gait cycle in a next walking of the user.

12. The walking assistance apparatus according to claim 11, further comprising:
   a first force sensor disposed on the first wire; and
   a second force sensor disposed on the second wire.

13. The walking assistance apparatus according to claim 1, further comprising:
   a rotation detector that detects a rotation direction of the user, wherein
   based on the rotation direction of the user and the gait information,
   the control circuit controls the first motor to reduce the length of the first wire and the second motor to reduce the length of the second wire at a predetermined timing.

14. The walking assistance apparatus according to claim 1, wherein
   if the first wire is longer than the second wire when the first motor and the second motor are not driven and the user is walking, the control circuit controls the first motor and the second motor to make the first wire longer than the second wire, and
   if the first wire is shorter than the second wire when the first motor and the second motor are not driven and the user is walking, the control circuit controls the first motor and the second motor to make the first wire shorter than the second wire.

15. A walking assistance apparatus comprising:
   a first wire including a first end and a second end;
   a second wire including a third end and a fourth end;
   a first motor connected to the first end;
   a second motor connected to the third end;
   a sensor; and
   a controller, wherein
   (a-1) the first motor and the second motor are included in a first belt to be worn around a knee of a first leg of a user, and the second end and the fourth end are fixed to a second belt to be worn around an ankle of the first leg or fixed to a shoe to be worn on the first leg, or
   (a-2) the first motor and the second motor are included in the second belt or the shoe, and the second end and the fourth end are fixed to the first belt,
   (b) the sensor detects a ground contact at an i-th time and at an (i+1)-th time after the i-th time, the ground contact being a change from a first state in which the first leg is separated from a ground to a second state in which the first leg is in contact with the ground, and the sensor does not detect the ground contact between the i-th time and the (i+1)-th time, where $1 \leq i \leq n$ where i is a natural number and n is a natural number greater than 1,
   (c) when the sensor detects the ground contact at the (i+1)-th time,
   (c-1) the controller controls the first motor to wind the first wire to make a first tension of the first wire between the first end and the first motor in a period from the (i+1)-th time to 40% or more and 60% or less of an average gait cycle be larger than a second tension of the first wire between the first end and the first motor at the (i+1)-th time, and
   (c-2) the controller controls the second motor to wind the second wire to make a third tension of the second wire between the third end and the second motor in the period from the (i+1)-th time to 40% or more and 60% or less of the average gait cycle be larger than a fourth tension of the second wire between the third end and the second motor at the (i+1)-th time, and
   (d) the average gait cycle is determined based on a difference between the (i+1)-th time and the i-th time.

* * * * *